(12) United States Patent
Rosenblatt

(10) Patent No.: US 10,918,276 B2
(45) Date of Patent: Feb. 16, 2021

(54) DIGITAL FUNDUS CAMERA

(71) Applicant: CAMEREYES LTD., Jerusalem (IL)

(72) Inventor: David Rosenblatt, Wilmington, DE (US)

(73) Assignee: CAMEREYES LTD., Jerusalem (IL)

( * ) Notice: Subject to any disclaimer, the term of this patent is extended or adjusted under 35 U.S.C. 154(b) by 0 days.

(21) Appl. No.: 16/978,681

(22) PCT Filed: Mar. 8, 2019

(86) PCT No.: PCT/IL2019/050260
§ 371 (c)(1),
(2) Date: Sep. 5, 2020

(87) PCT Pub. No.: WO2019/171388
PCT Pub. Date: Sep. 12, 2019

(65) Prior Publication Data
US 2021/0000342 A1    Jan. 7, 2021

(30) Foreign Application Priority Data

Mar. 8, 2018 (IL) .......................................... 257972

(51) Int. Cl.
*A61B 3/12* (2006.01)
*A61B 3/00* (2006.01)
*A61B 3/14* (2006.01)

(52) U.S. Cl.
CPC .............. *A61B 3/12* (2013.01); *A61B 3/0008* (2013.01); *A61B 3/14* (2013.01)

(58) Field of Classification Search
CPC ............ A61B 3/12; A61B 3/14; A61B 3/0008

USPC ................................. 351/206, 221, 246, 205
See application file for complete search history.

(56) References Cited

U.S. PATENT DOCUMENTS

| | | | |
|---|---|---|---|
| 3,594,071 | A | 7/1971 | Okajima |
| 4,422,736 | A | 12/1983 | Nunokawa |
| 6,404,985 | B1 | 6/2002 | Ohtsuka |
| 7,048,379 | B2 | 5/2006 | Miller et al. |
| 8,836,778 | B2 | 9/2014 | Ignatovich et al. |
| 9,060,718 | B2 | 6/2015 | Lawson et al. |
| 9,295,388 | B2 | 3/2016 | Lawson et al. |
| 2011/0085137 | A1 | 4/2011 | Kleen et al. |
| 2012/0092619 | A1 | 4/2012 | Rowe |

(Continued)

FOREIGN PATENT DOCUMENTS

| CN | 102641115 A | 8/2012 |
|---|---|---|
| WO | 2010/129775 A1 | 11/2020 |

OTHER PUBLICATIONS

International Search Report and Written Opinion of the ISA/EPO for PCT/IL2019/050260, dated Jun. 27, 2019.

*Primary Examiner* — Hung X Dang
(74) *Attorney, Agent, or Firm* — Novick, Kim & Lee, PLLC; Harold L. Novick

(57) ABSTRACT

Digital fundus cameras including an objective lens and a digital imager for capturing digital retinal images. The digital fundus cameras include an annular LED illumination arrangement having an annular LED illuminator with a ring of spaced apart individual masked LEDs, an annular folded illumination optical train and a multiple stage stray illumination trap arrangement for capturing stray illumination. The annular LED illumination arrangement can optically include a glare spot masking arrangement.

17 Claims, 17 Drawing Sheets

(56) References Cited

U.S. PATENT DOCUMENTS

2016/0128569 A1* 5/2016 Cheng ............... A61B 3/14
351/206
2018/0055351 A1 3/2018 Yates

* cited by examiner

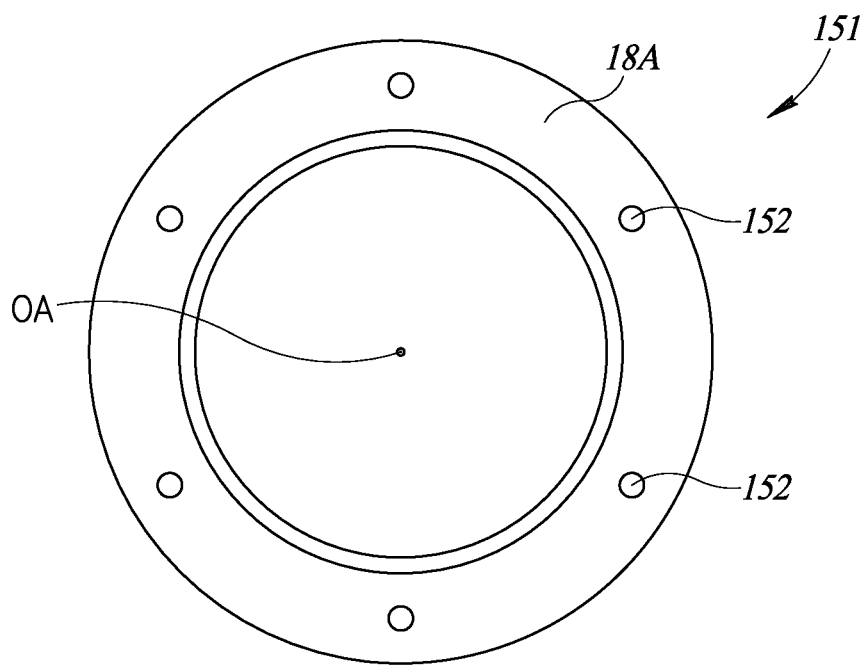
FIG. 7
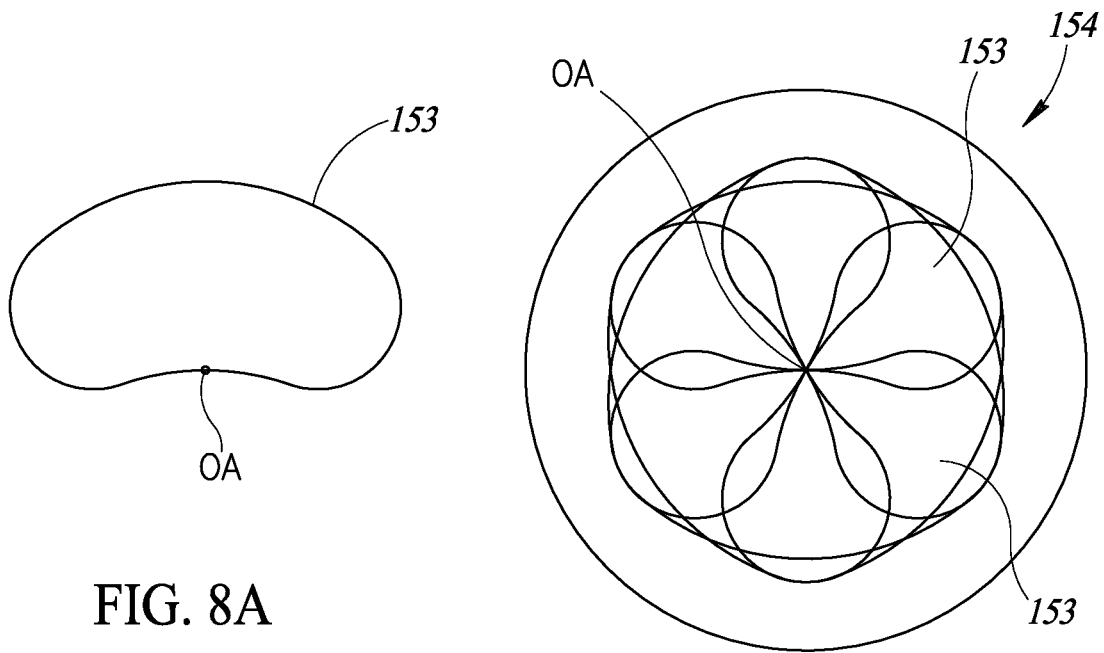
FIG. 8A
FIG. 8B

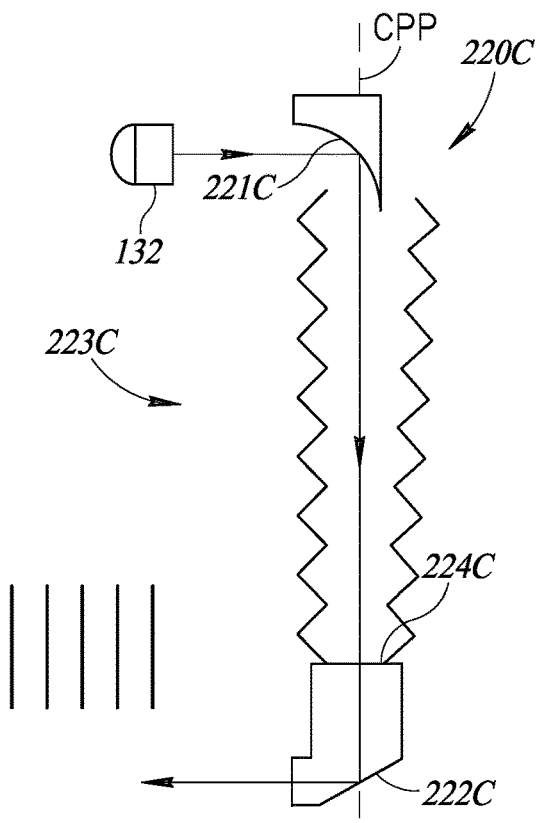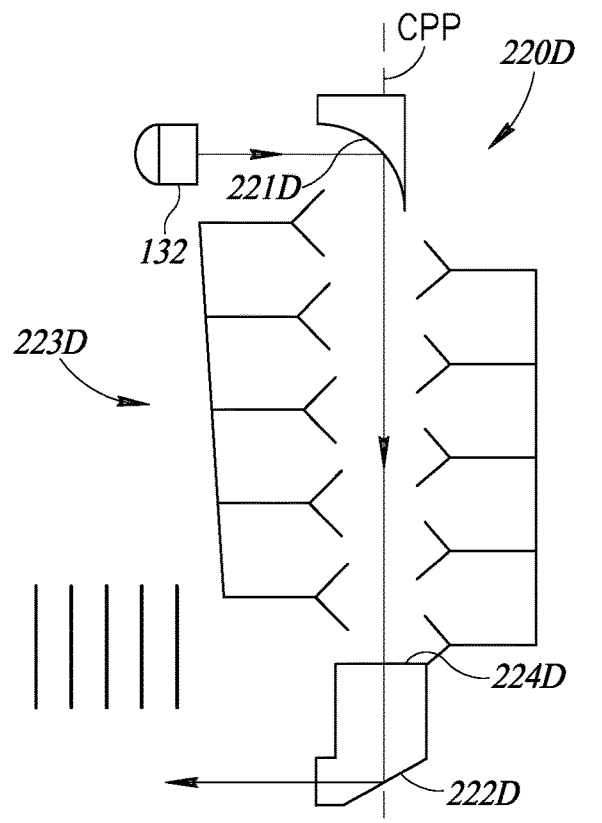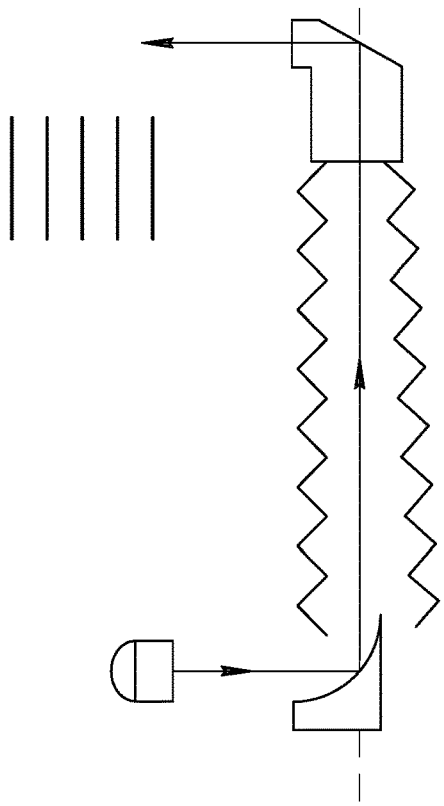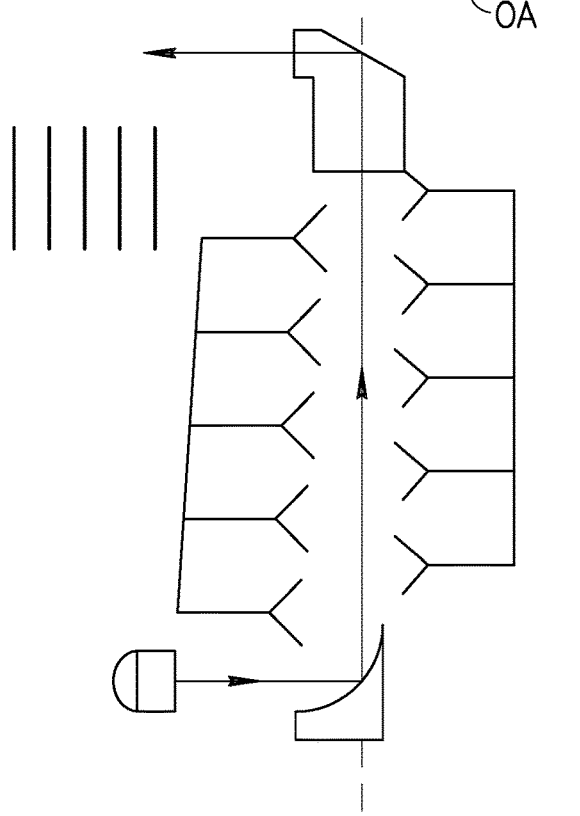
FIG. 16　　　　　　　　FIG. 17

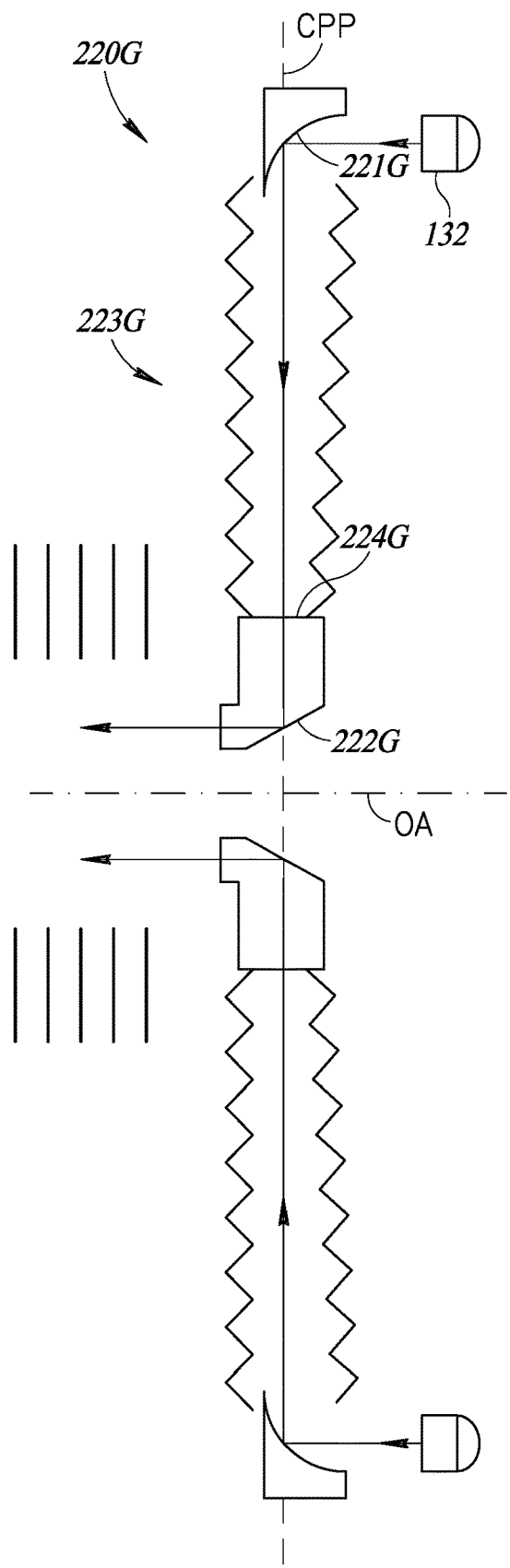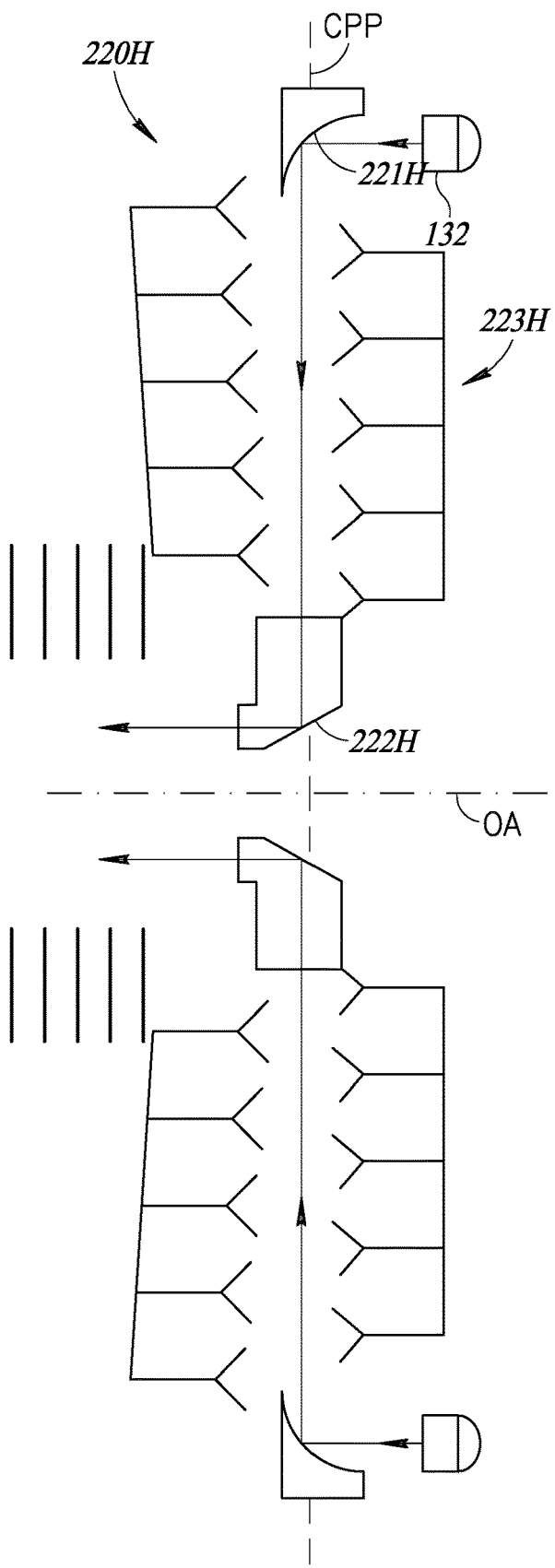
FIG. 20                    FIG. 21

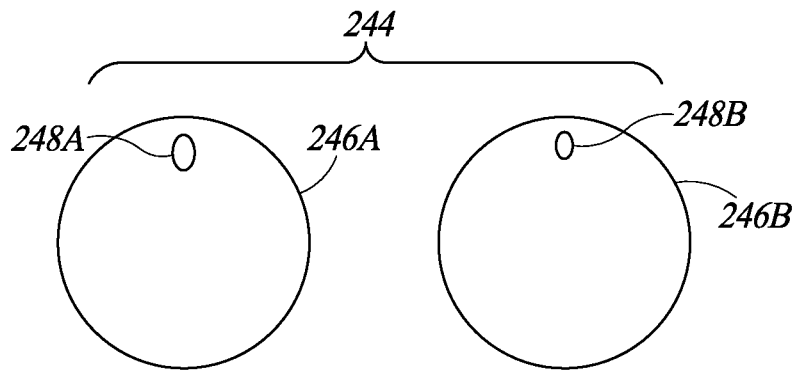
FIG. 23
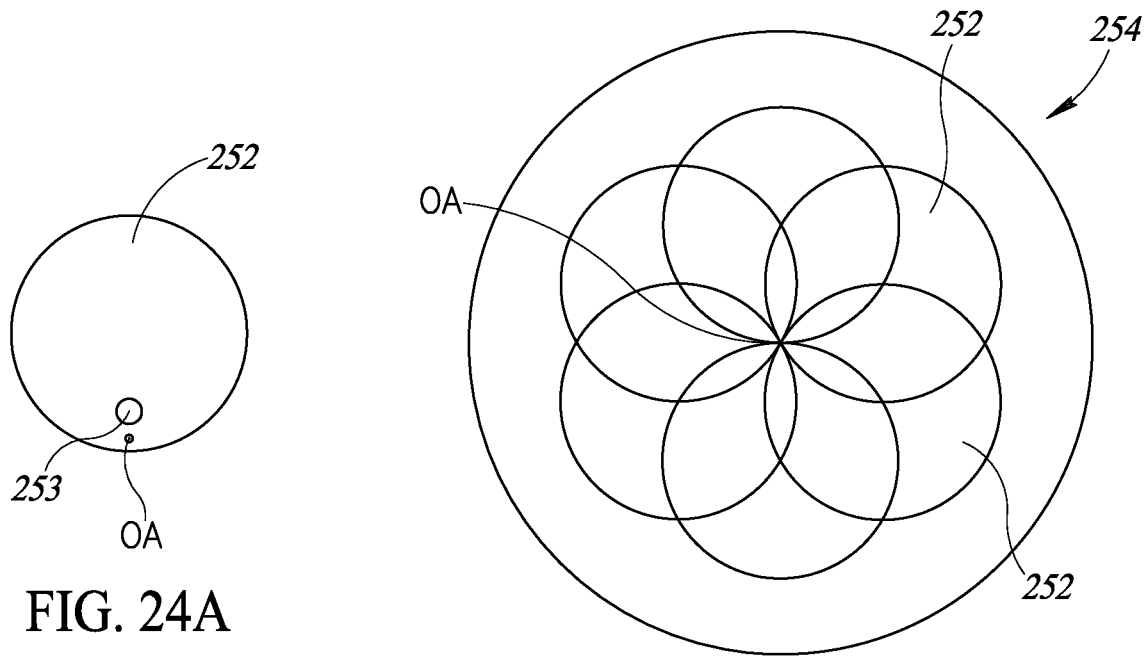
FIG. 24A
FIG. 24B

DIGITAL FUNDUS CAMERA

FIELD OF THE INVENTION

This present invention relates to digital fundus cameras.

BACKGROUND OF THE INVENTION

Digital fundus cameras include a rigid housing having an objective lens with an optical axis, an illumination annulus for illuminating a retinal region along an inbound illumination light path and a digital imager for capturing retinal images of the illuminated retinal region along an outbound image forming light path. Different ophthalmic clinical applications require retinal images at different image resolutions. Clinical grade retinal images are regarded as retinal images enabling visual distinction of pathologies such as micro aneurysms, intraretinal microvascular abnormalities (IRMA), and the like. Digital fundus cameras are preferably operative for imaging a retinal image in one or more imaging modes including inter alia mydriatic imaging and non-mydriatic imaging.

Retinal imaging is known to be challenging because of glare or reflex of inline illumination reflected from an objective lens in close proximity to an optical axis which appears as a bright spot in a digital retinal image. Conventional fundus cameras designed for use with photographic film went to great lengths to eliminate these reflex artifacts. Conventional fundus cameras used one or more glare spot masks as exemplified in inter alia U.S. Pat. No. 3,594,071 to Okajima. Some digital retinal imaging protocols include capturing a sequence of digital retinal images with a patient fixating his gaze in different directions thereby affording different views of his retina in each digital retinal image. Digital fundus cameras employ image processing for tiling multiple digital retinal images into a mosaic digital retinal image having a composite larger field of view than available from a single digital retinal image. Such image processing can be employed to remove glare from a mosaic digital retinal image and also defects from a single digital retinal image. Other digital retinal imaging protocols include capturing a single digital image which necessarily has to be void of glare or reflex.

Retinal imaging is also known to be challenging because retinas return only a small fraction of incident illumination, thereby requiring bright incident illumination for imaging purposes. But bright illumination militates against retinal imaging due to reflection and backscattering from an eye's anterior surfaces including its cornea and its natural lens that blinds a digital imager. Digital fundus cameras are designed to optimally separate between their inbound illumination light path and their outbound image forming light path. Accordingly, an ideal outbound image forming light path passes through an innermost pupillary center area in an open pupil and an ideal inbound illumination light path passes through an outermost pupillary annular surround peripheral to the innermost pupillary center area. The outermost pupillary annular surround is preferably separated from the innermost pupillary central area.

An objective lens has a working distance from an eye for imaging an eye's retinal surface as an imaged retina at a conjugate retinal plane and an eye's pupil as an imaged pupil at a conjugate pupillary plane. The digital imager is typically located along an optical axis and includes an imaging optical arrangement and an imaging sensor. The illumination annulus has a short radial length such that it can be disposed in the imaged outermost pupillary annular surround at the conjugate pupillary plane. Ideal digital fundus camera illumination requires an illumination envelope diverging from the conjugate pupillary plane towards the conjugate retinal plane such that its inner edge reaches the optical axis at the conjugate retinal plane and its outer edge reaches the boundary of the retinal region to be imaged. Such an illumination envelope ensures maximum separation for minimizing backscattering and glare. The illumination annulus intersects the eye's cornea at a larger diameter than the imaged pupil such that reflection from the sloping sidewalls of the cornea are mostly cast away and do not enter the digital imager. The illumination annulus converges from the pupil so that it intersects the optical axis at the retina resulting in a converging conical tunnel from the cornea to the pupil and posterior surface of the eye lens that is void of illumination for minimizing stray illumination which can backscatter and interfere with the outbound imaging forming light path and thereby cloud a digital retinal image.

Kohler illumination arrangements provide ideal fundus camera illumination for acquiring clinical grade retinal images but are relatively expensive and cumbersome. Kohler illumination arrangements use light sources such as filament bulbs or xenon flash lamps and an optical train of a condenser lens, a subfield condenser and an annular mirror for reflecting illumination along an inbound illumination light path for ensuring homogeneous illumination at a retinal region devoid of features from a filament. Kohler illumination arrangements typically additionally include an array of masks perpendicular to an illumination beam axis with apertures to shape the illumination beam and form a continuous illumination annulus of uniform brightness. Ideal fundus camera illumination requires a thin illumination annulus having a radial length that can be less than even 0.5 mm for non-mydriatic imaging of small pupils. Exemplary prior art includes inter alia U.S. Pat. No. 4,422,736 to Nunokawa entitled Eye Digital fundus camera Having Ring Slit Mask in Illuminating System.

More recent digital fundus camera illumination arrangements include an annular LED illuminator in the form of a ring of spaced apart individual masked LEDs for flash photography or mydriatic imaging with continuous illumination. U.S. Pat. No. 7,048,379 to Miller et al entitled Imaging Lens and Illumination System discloses such an annular LED illuminator. Individual masked LEDs have a high brightness diffusive phosphor coating which has a homogenizing effect to create an illumination pattern at a retina that is free of patterns from structures like bulb filaments. Digital fundus cameras use deflectors and/or polarizers to eliminate glare and backscattering but fail to achieve a thin illumination annulus and converging tunnel comparable to Kohler illumination arrangements. LED illumination based digital fundus cameras are more compact and less expensive than digital fundus cameras with Kohler illumination arrangements but are generally considered incapable of capturing clinical grade retinal images due to non-ideal fundus camera illumination. Such digital fundus cameras can also include IR LEDs for continuous non-mydriatic imaging prior to flash image capture without pupil dilation.

There is a need for digital fundus cameras with an annular LED illuminator for providing ideal fundus camera illumination for acquiring clinical grade retinal images.

SUMMARY OF THE INVENTION

Generally speaking, the present invention is directed towards digital fundus cameras for providing ideal digital fundus camera illumination for acquiring clinical grade retinal images. The digital fundus cameras of the present invention have the same basic construction as hitherto described digital fundus cameras and additionally include an annular LED illumination arrangement incorporating a multiple stage stray illumination trap for progressively capturing stray illumination light from an annular LED illuminator such that its incident illumination towards an eye is bound within an illumination envelope conforming to the requirements of ideal fundus camera illumination. Some annular LED illumination arrangements leave a glare spot on an objective lens whilst other annular LED illumination arrangements additionally include a glare spot masking arrangement to remove glare or reflex from an objective lens. The former are intended to be used with conventional image processors for tiling multiple digital retinal images into a mosaic digital retinal image having a composite larger field of view than available from a single digital retinal image and remove glare or reflex therefrom and also defects from single digital retinal images. Glare spot masking arrangement can include one or more glare spot masks.

For illustrative purposes, LED illumination is described in connection with a LED commercially available from Cree, Inc. 4600 Silicon Drive, Durham, N.C. 27703 www.cree.com, namely, the XLamp XQ-E LED. The XLamp XQ-E LED emits a wide solid angle illumination beam approaching near $2\pi$ steradian abbreviated to $2\pi$ sr (see FIG. 4). The XLamp XQ-E LED emits its near $2\pi$ sr illumination beam with a typical largely bell shaped luminous intensity as a function of illumination emission angle (see FIG. 5).

The multiple stage stray illumination traps of the present invention, due to the limitations of etendue or the optical invariant, ensure that each individual LED's near $2\pi$ solid angle illumination beam is emitted as a narrow solid angle illumination beam with an illumination emission solid angle of about 0.03 sr. Taking into account a LED's weighted angular emitted power distribution, an imaged LED emits a mere between 1% to 2% of its object LED's illumination emission meaning that up to 99% of its illumination emission is required to be absorbed and prevented from escaping at undesirable angles into an inbound illumination light path towards an eye. Accordingly, for a ring of, say, twelve spaced apart individual masked LEDs each emitting 185 mW of illumination emission, a multiple stage stray illumination trap of the present invention is required to contain and absorb more than 2 W of illumination emission. The multiple stage stray illumination traps of the present invention preferably include a stray illumination trap between each consecutive pair of optical elements in an optical train from an annular LED illuminator to an objective lens to achieve such absorption.

The stray illumination traps have structured surfaces with high aspect ratio grooves or cavities coated with a black highly illumination light absorbing coating. The cavities preferably have aspect ratios of depth to width of the groove or cavity that allow for multiple reflections within a cavity of preferably six or more reflections such that there are sufficient reflections to reduce illumination escaping a cavity to less than 2% of the original stray illumination. Such an aspect ratio ensures sufficient absorption of original stray illumination entering a cavity at a small acute angle which might otherwise compromise reflectance of a black coating such that only 50% illumination is absorbed per reflection compared to a large acute angle. Stray illumination traps employing such structured surfaces thereby create large stray light illumination trapping surface areas in the small available volume of a digital fundus camera housing for progressively and accumulatively capturing almost the entire illumination emission from an annular LED illumination arrangement except for a ring of narrow solid angle illumination beams imaged at a conjugate pupillary plane. The high aspect ratio cavities of the stray illumination trapping surfaces can be fabricated by assembly of plates and spacers with different diameter, or by imprinting, replication or subtractive machining processing. The structured surfaces can be preprocessed on a flexible substrate and curled or deformed into a final desired shape.

Some preferred embodiments of an annular LED illumination arrangement include a monolithic plastic component having an integral primary focusing reflector and an integral secondary reflector. Other preferred embodiments of an annular LED illumination arrangement include a discrete primary focusing reflector and a discrete secondary reflector. Components can be injection molded as a single part or made by bonding several molded parts. Suitable plastic materials include inter alia PMMA, polystyrene, polycarbonate and the like. The digital fundus cameras of the present invention can be implemented as tabletop eye examination apparatus, handheld eye examination apparatus, goggles, and the like.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which:

FIG. 7 is a schematic view of an annular LED illuminator image at the digital fundus camera's conjugate pupillary plane;

FIG. 8A is a schematic view of a broad bean shaped illumination patch originating from a 12 o'clock located masked LED at the digital fundus camera's conjugate retinal plane;

FIG. 8B is a schematic view of an overall illumination pattern image at the digital fundus camera's conjugate retinal plane;

FIG. 16 is a schematic diagram of an eighth embodiment of an annular LED illumination arrangement with illustrative optical rays;

FIG. 17 is a schematic diagram of a ninth embodiment of an annular LED illumination arrangement with illustrative optical rays;

FIG. 20 is a schematic diagram of a twelfth embodiment of an annular LED illumination arrangement with illustrative optical rays;

FIG. 21 is a schematic diagram of a thirteenth embodiment of an annular LED illumination arrangement with illustrative optical rays;

FIG. 23 is a schematic front view of glare spot masks of a glare spot masking arrangement of FIG. 22's glare spot free annular LED illumination arrangement;

FIG. 24A is a schematic view of a circular illumination patch originating from a 12 o'clock deployed masked LED of a glare spot free annular LED illumination arrangement at a digital fundus camera's conjugate retinal plane;

FIG. 24B is a schematic view of an overall illumination pattern image of a glare spot free annular LED illumination arrangement at a digital fundus camera's conjugate retinal plane.

DETAILED DESCRIPTION OF THE DRAWINGS

Figure 1:
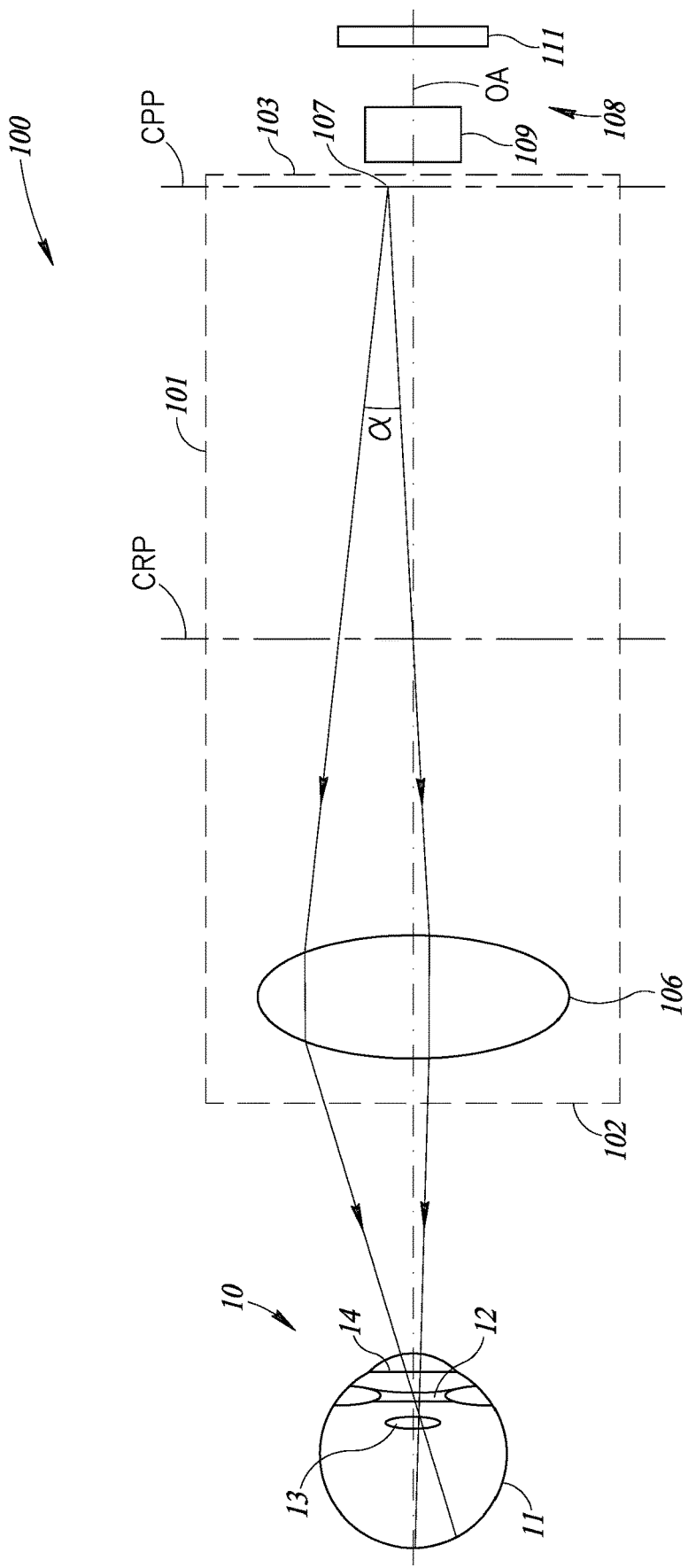
FIG. 1 is an optical ray diagram of an ideal inbound illumination light path of a digital fundus camera for illuminating a retinal region.
Figure 2:
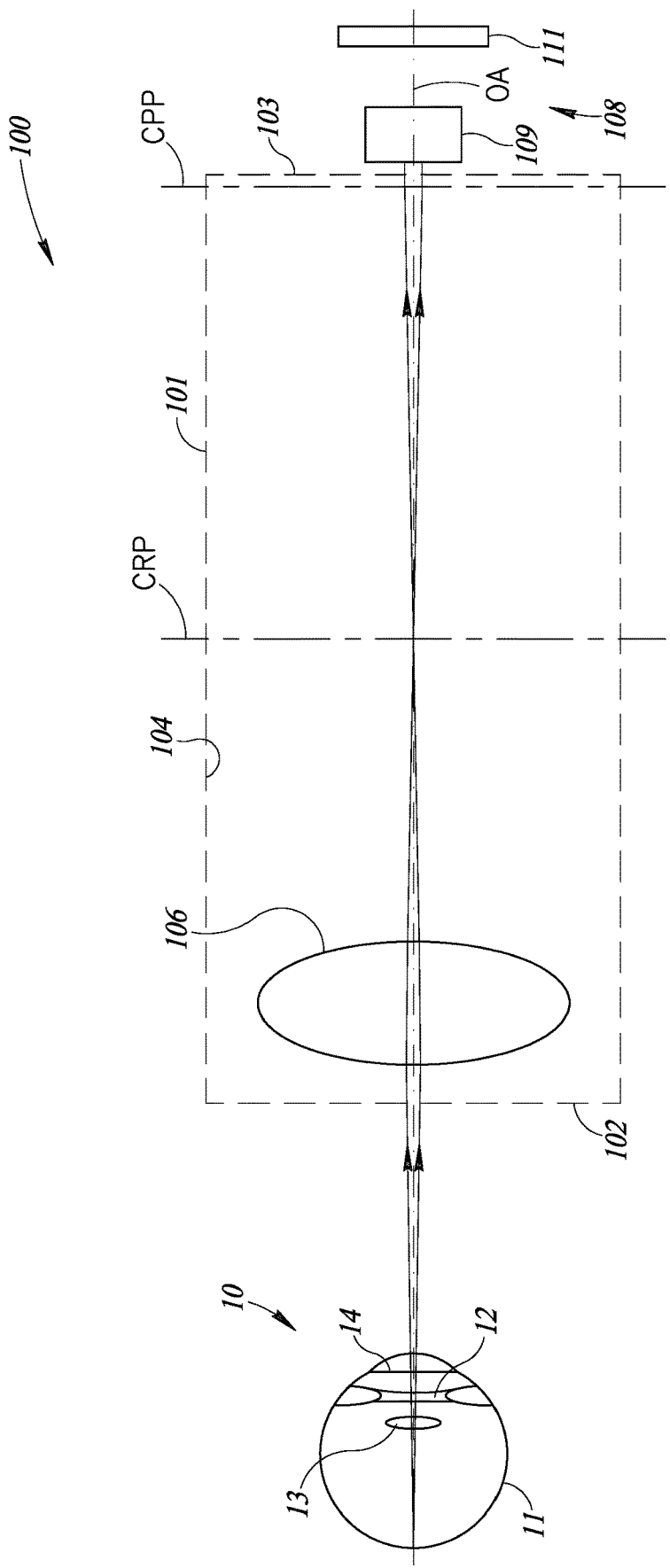
FIG. 2 is an optical ray diagram of an ideal outbound image forming light path of a digital fundus camera for capturing a digital retinal image of an illuminated retinal region.
Figure 3:
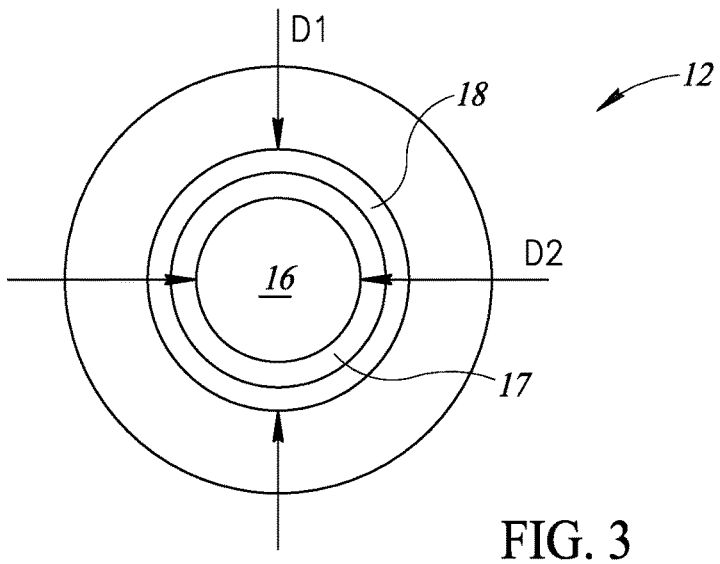
FIG. 3 is a schematic front view of an eye including a concentric arrangement of an innermost pupillary central area, an intermediate annular spacer and an outermost pupillary annular surround.

Digital Fundus Camera Construction with Ideal Inbound Illumination Light Path and Ideal Outbound Image Forming Light Path FIG. 1 and FIG. 2 show an eye 10 having a retina 11, a pupil 12, a lens 13 and a cornea lens 14, and a digital fundus camera 100 for imaging an illuminated retinal region. FIG. 3 shows the eye 10 includes a concentric arrangement of an innermost pupillary central area 16, an intermediate pupillary annular spacer 17 and an outermost pupillary annular surround 18. The pupil 12 has an outermost pupil diameter D1 of about 4 mm. The innermost pupillary central area 16 has a diameter D2 of between 2 mm to 2.5 mm. The outermost pupillary annular surround 18 has a radial thickness of about 0.5 mm. The dimensions are measured from being observed externally to the eye.

The digital fundus camera 100 includes a rigid tubular digital fundus camera housing 101 having a leading housing end 102, a trailing housing end 103 and an inside housing surface 104. The digital fundus camera 100 has an objective lens 106 towards the leading housing end 102. The objective lens 106 has an optical axis OA and a working distance from an eye. The objective lens 106 can be a plano-convex aspheric lens as shown or a dual convex aspheric lens. The objective lens 106 can be a cemented achromat or a simple lens. The objective lens 106 images the eye's retinal surface as a retinal image at a conjugate retinal plane CRP and its pupil as a pupil image at a conjugate pupillary plane CPP perpendicular to the optical axis OA, respectively. The digital fundus camera 100 employs an illumination annulus 107 with a small radial length at the conjugate pupillary plane CPP for illuminating a retinal region. The digital fundus camera 100 includes a digital imager 108 for capturing digital retinal images of a retinal region through the illumination annulus 107. The digital imager 108 includes a secondary imaging optical arrangement 109 and an imaging sensor 111.

The illumination annulus 107 diverges from the conjugate pupil plane CPP at an illumination emission divergence angle α towards the conjugate retinal plane CRP such that, at the conjugate retinal plane CRP, the illumination annulus's inner edge reaches the optical axis OA and its outer edge reaches the boundary of the retinal region to be imaged. The illumination annulus 107 converges from the objective lens 106 towards the eye 10 such that it intersects the eye's cornea lens 14 at a larger diameter than the pupil image such that reflection from the sloping sidewalls of the cornea lens 14 are mostly cast away from the eye 10. The illumination annulus 107 further converges from the pupil 12 to intersect the optical axis OA at the retina 11 resulting in a dark or non-illuminated converging conical tunnel from the cornea to the pupil and posterior surface of the eye lens.

Figure 4:
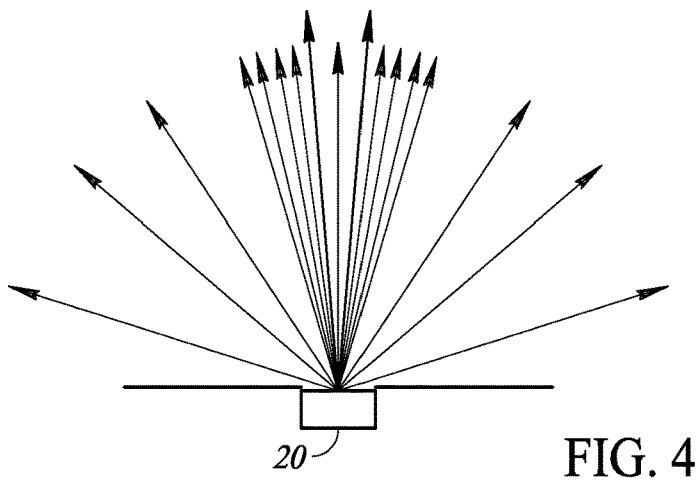
FIG. 4 is a schematic diagram of a masked LED emitting a near $2\pi$ steradian wide solid angle illumination beam.

FIG. 4 shows an exemplary masked LED 20 emitting a near 2π steradian wide solid angle illumination beam.

Figure 5:
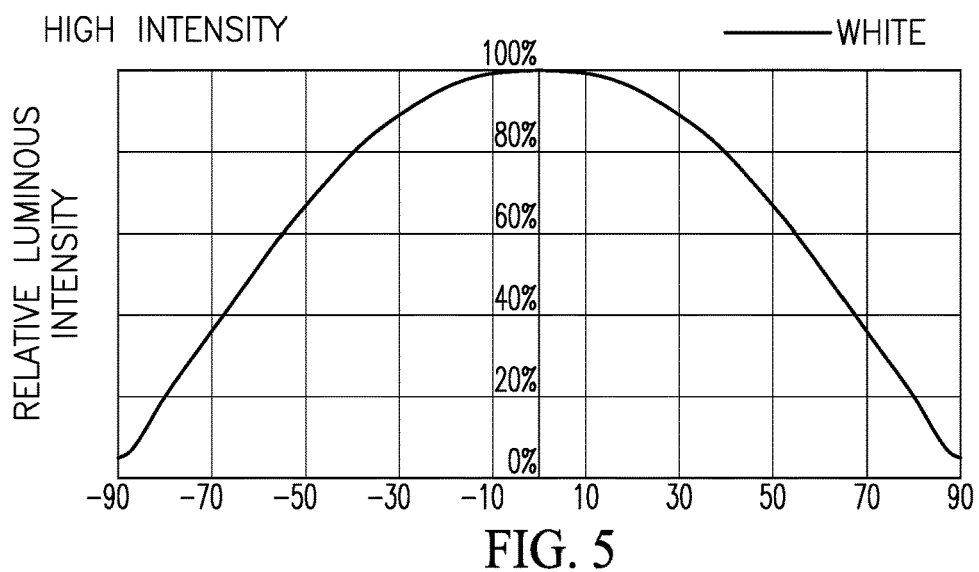
FIG. 5 is a graph of luminous intensity of FIG. 4's masked LED as a function of illumination emission angle.

FIG. 5 shows FIG. 4's illumination beam has a typical largely bell shaped luminous intensity as a function of illumination emission angle.

Basic Annular LED Illumination Arrangements

Figure 6:
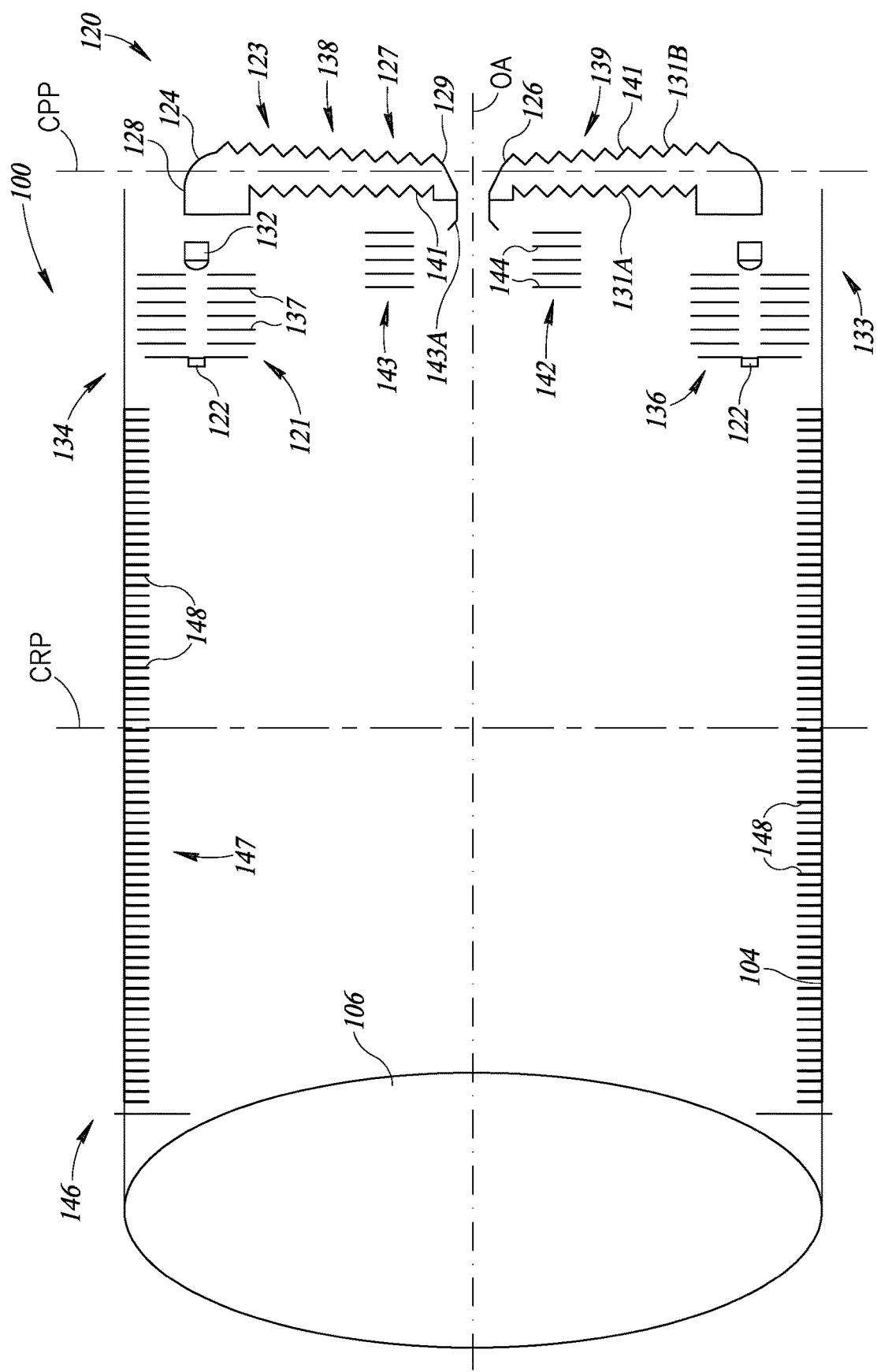
FIG. 6 is a schematic view of a digital fundus camera with a first embodiment of an annular LED illumination arrangement.

FIG. 6 shows the digital fundus camera 100 includes an annular LED illumination arrangement 120 at the trailing housing end 103. The annular LED illumination arrangement 120 provides ideal fundus camera illumination along an inbound illumination light path for ensuring clinical grade retinal images. The annular LED illumination arrangement 120 includes an annular LED illuminator 121 emitting illumination co-directional with the optical axis OA and spaced apart therefrom in an opposite direction to the objective lens 106. The annular LED illuminator 121 is in the form of a ring of spaced apart individual masked LEDs 122 each emitting a wide solid angle illumination beam. The wide solid angle illumination beams can have different cross-sections transverse to their emission direction including inter alia circular, ellipsoidal, and the like.

The annular LED illumination arrangement 120 includes an annular folded illumination optical train 123 centered on the optical axis OA and perpendicular thereto. The annular folded illumination train 123 includes a primary focusing reflector 124 focusing illumination towards a secondary reflector 126 for reflecting illumination towards the objective lens 106.

The primary focusing reflector 124 is preferably implemented as a single reflector for the entire annular LED illuminator 121. Alternatively, the primary focusing reflector 124 can be implemented as a multitude of primary focusing reflectors in individual registration with the masked LEDs 122. The primary focusing reflector 124 has an aspherical cross section in a longitudinal cross section of the digital fundus camera 100 along the optical axis OA for focusing the illumination beams from the annular LED illuminator 121. The primary focusing reflector 124 can employ total internal reflection or mirror coatings.

The secondary reflector 126 is preferably implemented as a single conical reflector for the entire annular LED illuminator 121. Alternatively, the secondary reflector 126 can be implemented as a multitude of secondary reflectors in individual registration with the masked LEDs 122. A single conical reflector is easier to fabricate than a multi-faceted secondary reflector and allows a higher density of LED images without limitation of a minimum facet size due to manufacturing constraints.

The annular folded illumination optical train 123 is constituted by an annular monolithic plastic component 127 having an outside rim surface 128 generally co-directional with the optical axis OA, an inside rim surface 129 generally co-directional with the optical axis OA and an opposite pair of annular major surfaces 131 extending between the outside rim surface 128 and the inside rim surface 129 and generally perpendicular to the optical axis OA. The outside rim surface 128 is formed with the primary focusing reflector 124. The inside rim surface 129 is formed with the secondary reflector 126. The opposite pair of annular major surfaces 131 includes a leading annular major surface 131A facing the leading housing end 102 and a trailing annular major surface 131B facing the trailing housing end 103. The opposite pair of annular major surfaces 131 converge from the outside rim surface 128 to the inside rim surface 129. The annular monolithic plastic component 127 can be formed from suitable plastic materials including inter alia PMMA, polystyrene, polycarbonate, and the like.

The annular LED illumination arrangement 120 includes an annular arrangement of refractive mini-lenses 132 in registration with the ring of spaced apart individual masked LEDs 122 and disposed between the annular LED illuminator 121 and the annular folded illumination optical train 123 for collecting illumination towards the primary focusing reflector 124 such that the annular arrangement of refractive mini-lenses 132 and the primary focusing reflector 124 together create LED images at the secondary reflector 126.

The annular LED illumination arrangement 120 includes a multiple stage stray illumination trap arrangement 133 for ensuring that the annular LED illuminator 121 is imaged at the conjugate pupillary plane CPP as small illumination sources each emitting a narrow solid angle illumination beam for illuminating a section of the retinal region to be imaged.

The multiple stage stray illumination trap arrangement 133 preferably includes a first stage trap 134 disposed between the annular LED illuminator 121 and the annular arrangement of refractive mini-lenses 132 for capturing stray illumination from the inbound illumination light path emitted by the annular LED illuminator 121. The first stage trap 134 includes a ring of baffle tubes 136 co-directional with the optical axis OA and in registration with the ring of spaced apart masked LEDs 122. Each baffle tube 136 includes a stack of staggered annular baffles 137 having a black highly light absorbing coating for absorbing stray illumination. Suitable black highly light absorbing coatings include inter alia Black Metal Velvet commercially available from Acktar Corporation www.acktar.com The multiple stage stray illumination trap arrangement 133 preferably includes a second stage trap 138 centered on the optical axis OA and disposed between the primary focusing reflector 124 and the secondary reflector 126 for capturing stray illumination from the inbound illumination light path reflected by the primary focusing reflector 124. The second stage trap 138 is constituted by the opposite pair of annular major surfaces 131 preferably having the same coating as the baffle tubes 136 and being formed with baffle arrangements 139 of concentric ridged surfaces 141.

The multiple stage stray illumination trap arrangement 133 preferably includes a third stage trap 142 for capturing stray illumination at the exit of the illumination beams from the annular LED illumination arrangement 120 towards the objective lens 106. The third stage trap 142 includes a baffle tube 143 centered on the optical axis OA. The baffle tube 143 includes a stack of staggered annular baffles 144 preferably having the same coating as the baffle tubes 136. The baffle tube 143 further includes a thin cylindrical deflector flange 143A bounding the inside rim surface 129 and extending from the secondary reflector 126 towards the objective lens 106. The deflector flange 143A is angled outwards with respect to the optical axis OA to deflect stray illumination beyond the intended illumination emergence divergence angle α to the baffles 144 for absorption therein.

The digital fundus camera 100 preferably includes a supplementary stray illumination trap 146 in addition to the multiple stage stray illumination trap arrangement 133 implemented by the inside housing surface 104 having a stack of staggered annular baffles 147 centered on the optical axis OA. The stack of staggered annular baffles 147 preferably has the same coating as the baffle tubes 136. The stack of staggered annular baffles 147 form annular cavities 148 for cleaning up the exterior angles of the illumination beams and reflections from the objective lens 106.

FIG. 7 shows an annular LED illuminator image 151 of the annular LED illuminator 121 at the conjugate pupillary plane CPP at the outermost pupillary annular surround image 18A. The annular LED illuminator image 151 includes a ring of spaced apart bright patches 152 corresponding to images of the masked LEDs 122 as opposed to a continuous illumination annulus of a Kohler illumination arrangement. Each masked LED 122 results in a broad bean shaped illumination patch 153 at the conjugate retinal plane CRP and the imaged retinal region. FIG. 8A shows the broad bean shaped illumination patch 153 illuminated from a 12 o'clock located masked LED 122 at the conjugate retinal plane CRP. The other masked LEDs 122 illuminate overlapping retinal areas according to their positions relative to the 12 o'clock masked LED 122 resulting in an overall illumination pattern image 154 as shown in FIG. 8B.

Figure 9:
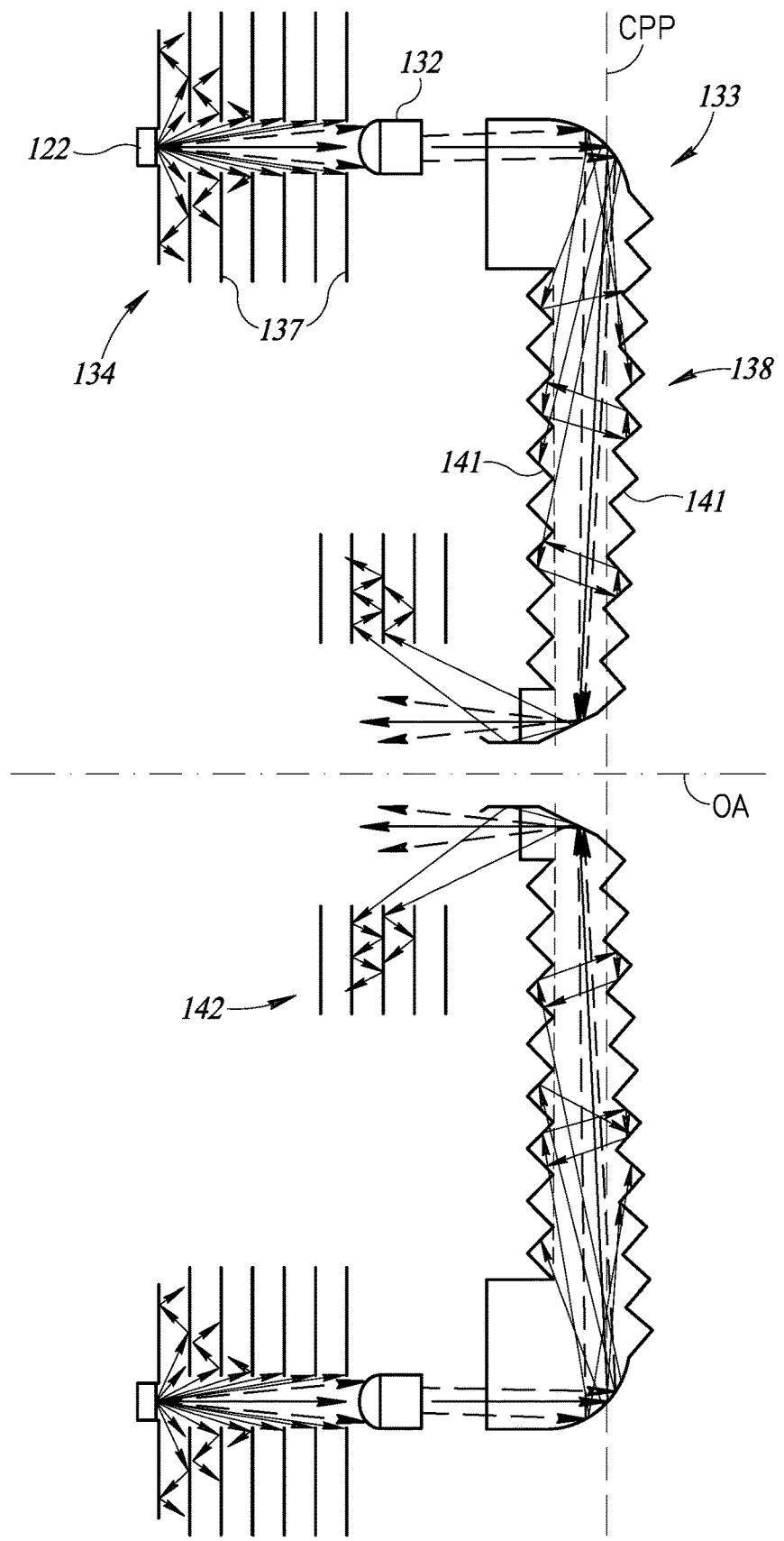
FIG. 9 is a schematic diagram of the first embodiment of the annular LED illumination arrangement with illustrative optical rays.

FIG. 9 shows the operation of the multiple stage stray illumination trap 133 for progressively capturing additional stray illumination light from the inbound illumination light path. The first stage trap 134 ensures that illumination light beyond the intended inbound illumination light path is captured between adjacent baffles 137. Absorption of the stray illumination can occur after a single reflection or multiple reflections. The first stage trap 134 is intended to capture the majority of the stray illumination from the inbound illumination light path. The second stage trap 138 ensures illumination light beyond the intended inbound illumination light path is captured by the concentric ridged surface 141. Absorption of the stray illumination can occur after a single reflection or multiple reflections. The third stage trap 142 is intended to capture the remaining stray illumination from the inbound illumination light path.

FIG. 10 to FIG. 13 show additional annular LED illumination arrangements each including an annular monolithic plastic component acting as a folded illumination optical train.

Figure 10:
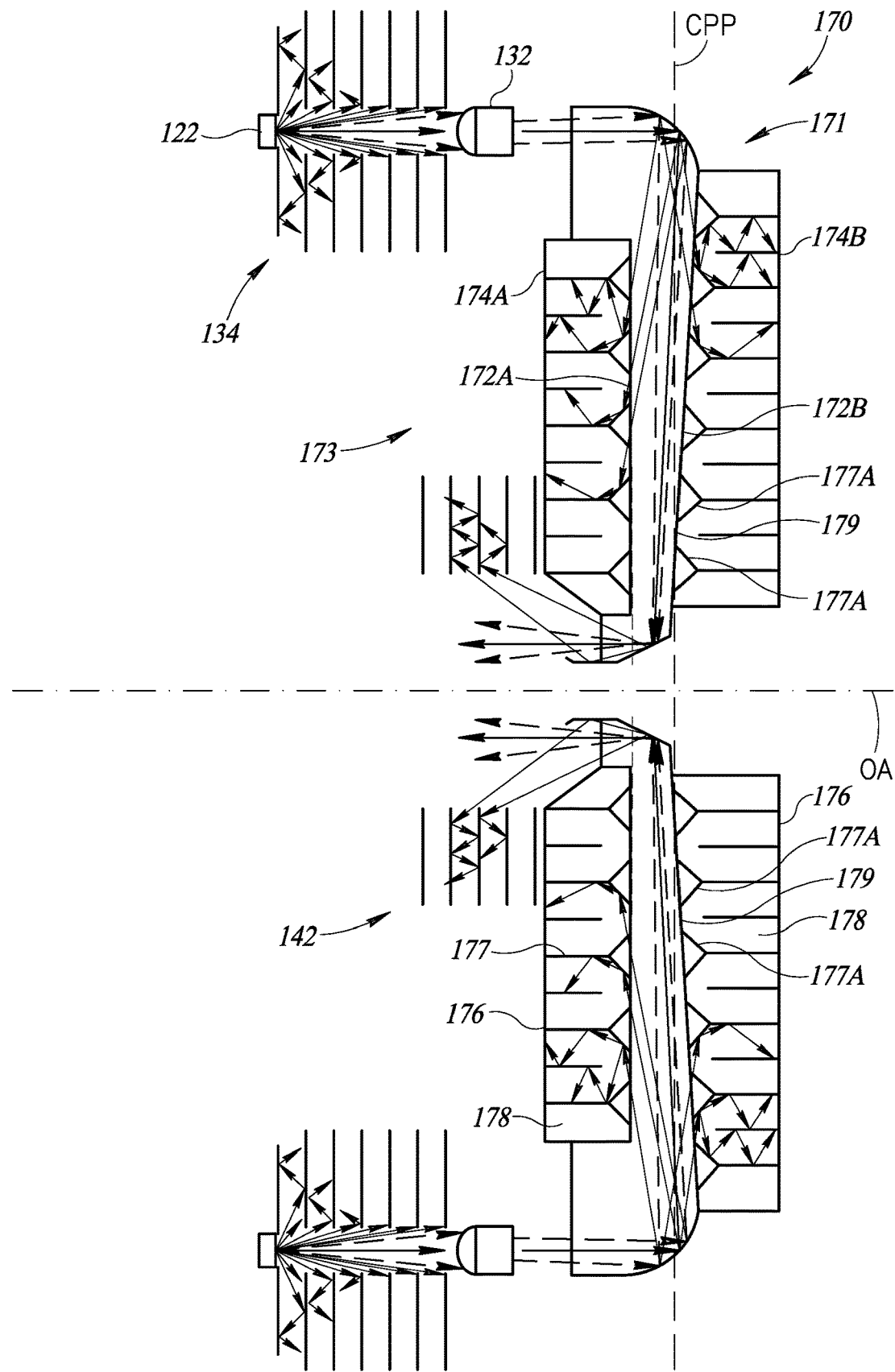
FIG. 10 is a schematic diagram of a second embodiment of an annular LED illumination arrangement with illustrative optical rays.

FIG. 10 shows an annular LED illumination arrangement 170 differing from the annular LED illumination arrangement 120 insofar as the latter 170 includes an annular monolithic plastic component 171 with an opposite pair of planar annular major surfaces 172 including a leading planar annular major surface 172A and a trailing planar annular major surface 172B. The latter 170 includes a second stage trap 173 constituted by an opposite pair of baffle arrangements 174 in the form of annular baffle devices mounted on the opposite pair of planar annular major surfaces 172. The opposite pair of annular baffle devices 174 includes a leading annular baffle device 174A mounted on the leading planar annular major surface 172A and a trailing annular baffle device 174B mounted on the trailing planar annular major surface 172B. The annular baffle devices 174 each include an annular base plate 176 centered on the optical axis OA and having a series of concentric fins 177 directed to a planar annular major surface 172 thereby forming a series of concentric compartments 178 therebetween. The series of concentric fins 177 is preferably divided into adjacent fin pairs having their free edges 177A disposed towards one another thereby forming annular narrow entrances 179 into the concentric compartments 178 thereby facilitating trapping stray illumination light inside the compartments 178.

Figure 11:
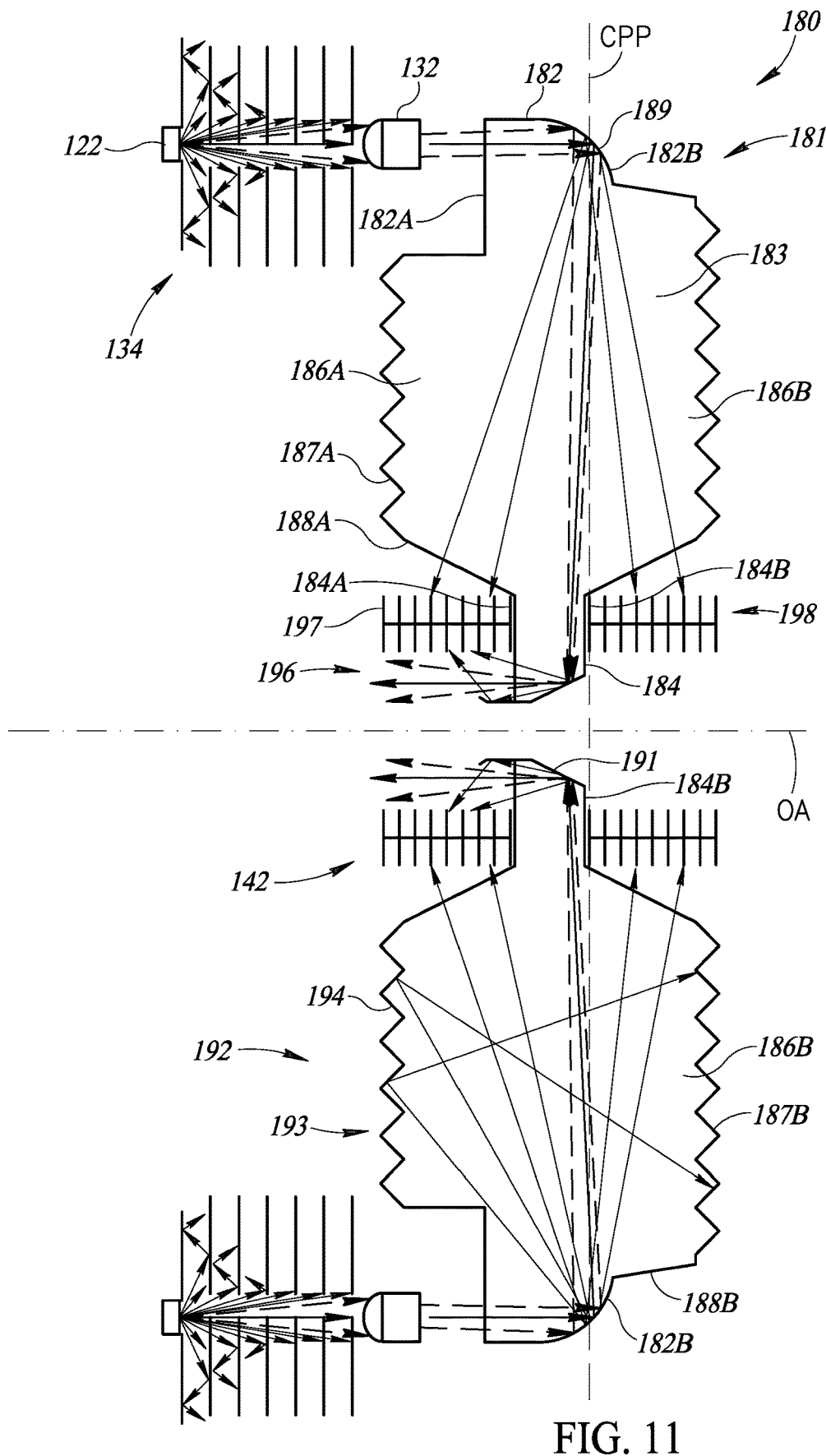
FIG. 11 is a schematic diagram of a third embodiment of an annular LED illumination arrangement with illustrative optical rays.

FIG. 11 shows an annular LED illumination arrangement 180 differing from the annular LED illumination arrangement 120 insofar as the latter 160 includes an annular monolithic plastic component 181 having an outside flange 182, an intermediate illumination venting section 183 and an inside flange 184. The outside flange 182 has a leading outside flange surface 182A facing the objective lens 106 and a trailing outside flange surface 182B facing away from the objective lens 106. The inside flange 184 has a leading inside flange surface 184A facing the objective lens 106 and a trailing inside flange surface 184B facing away from the objective lens 106.

The intermediate illumination venting section 183 includes a leading truncated conical shaped illumination vent 186A having a leading annular major surface 187A perpendicular to the optical axis OA and a leading peripheral surface 188A extending between the leading annular major surface 187A and the leading outside flange surface 182A and the leading inside flange surface 184A. The intermediate illumination light venting section 183 includes a trailing truncated conical shaped illumination vent 186B having a trailing annular major surface 187B perpendicular to the optical axis OA and a trailing peripheral surface 188B extending between the trailing annular major surface 187B and the trailing outside flange surface 182B and the trailing inside flange surface 184B. The trailing outside flange surface 182B has an aspherical surface acting as a primary focusing reflector 189 and the inside flange 184 includes a conical surface between the leading inside flange surface 184A and the trailing inside flange surface 184B acting as a secondary reflector 191.

The annular LED illumination arrangement 180 includes a second stage trap 192 constituted by the opposite pair of annular major surfaces 187 preferably having the same coating as the baffle tubes 136 and formed with baffle arrangements 193 of concentric ridged surfaces 194. The second stage trap 192 also involves stray illumination from the inbound illumination light path exiting from the intermediate illumination venting section 183 through the opposite pair of peripheral surfaces 188 into the digital fundus camera housing 101 for subsequent absorption therein.

The annular LED illumination arrangement 180 additionally includes a third stage trap 196 similar to the third stage trap 142 and additionally includes a stack of staggered annular baffles 197 facing the leading truncated conical shaped illumination vent 186A for absorption stray illumination vented therefrom. The annular LED illumination arrangement 180 can additionally include a duplicate third stage trap 198 centered on the optical axis OA and opposite the third stage trap 196 for absorbing stray illumination vented from the trailing truncated conical shaped illumination vent 186B.

Figure 12:
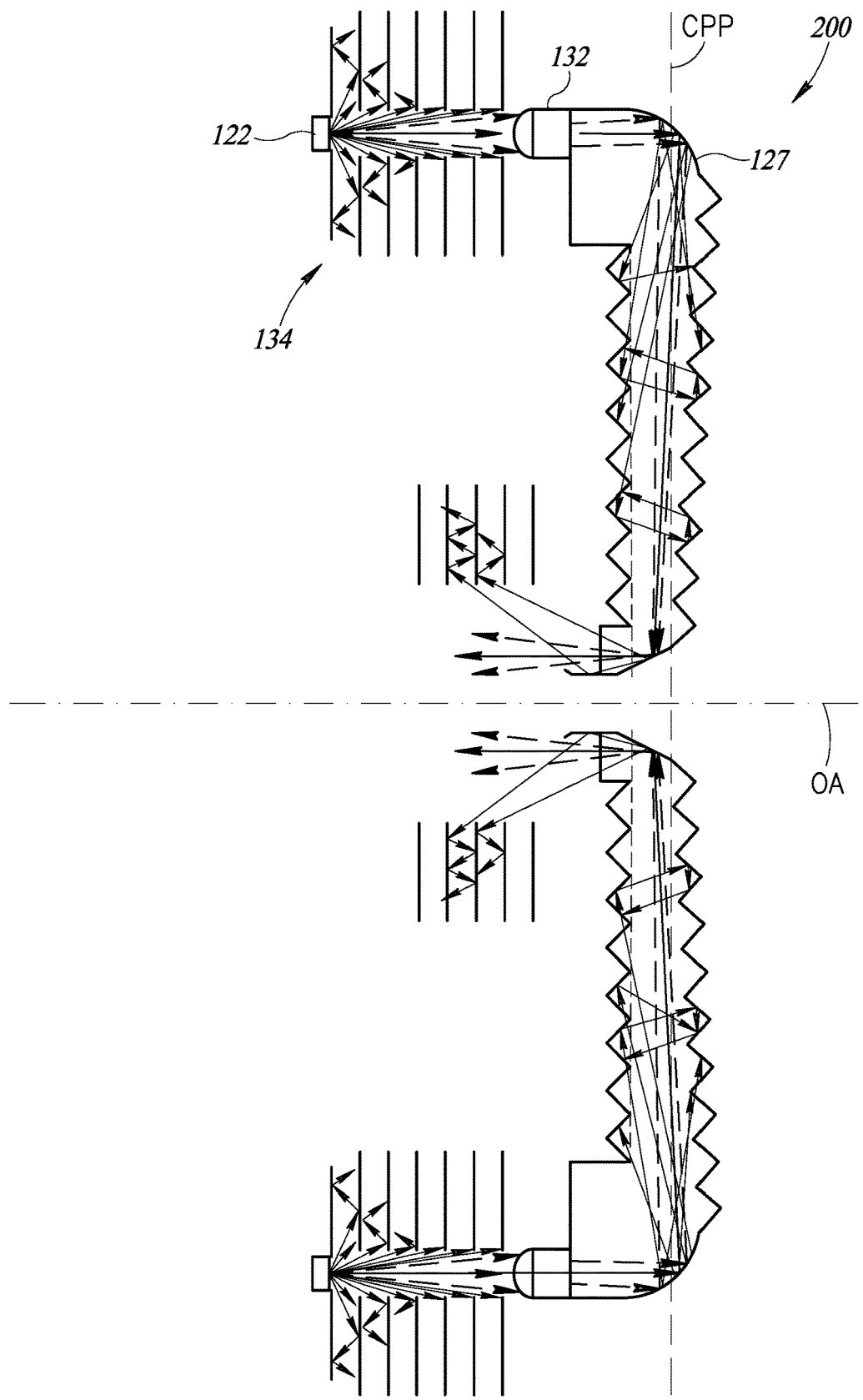
FIG. 12 is a schematic diagram of a fourth embodiment of an annular LED illumination arrangement with illustrative optical rays.

FIG. 12 shows an annular LED illumination arrangement 200 differing from the annular LED illumination arrangement 120 insofar as the latter 200's annular monolithic plastic component 127 additionally includes the annular arrangement of refractive mini-lenses 132.

Figure 13:
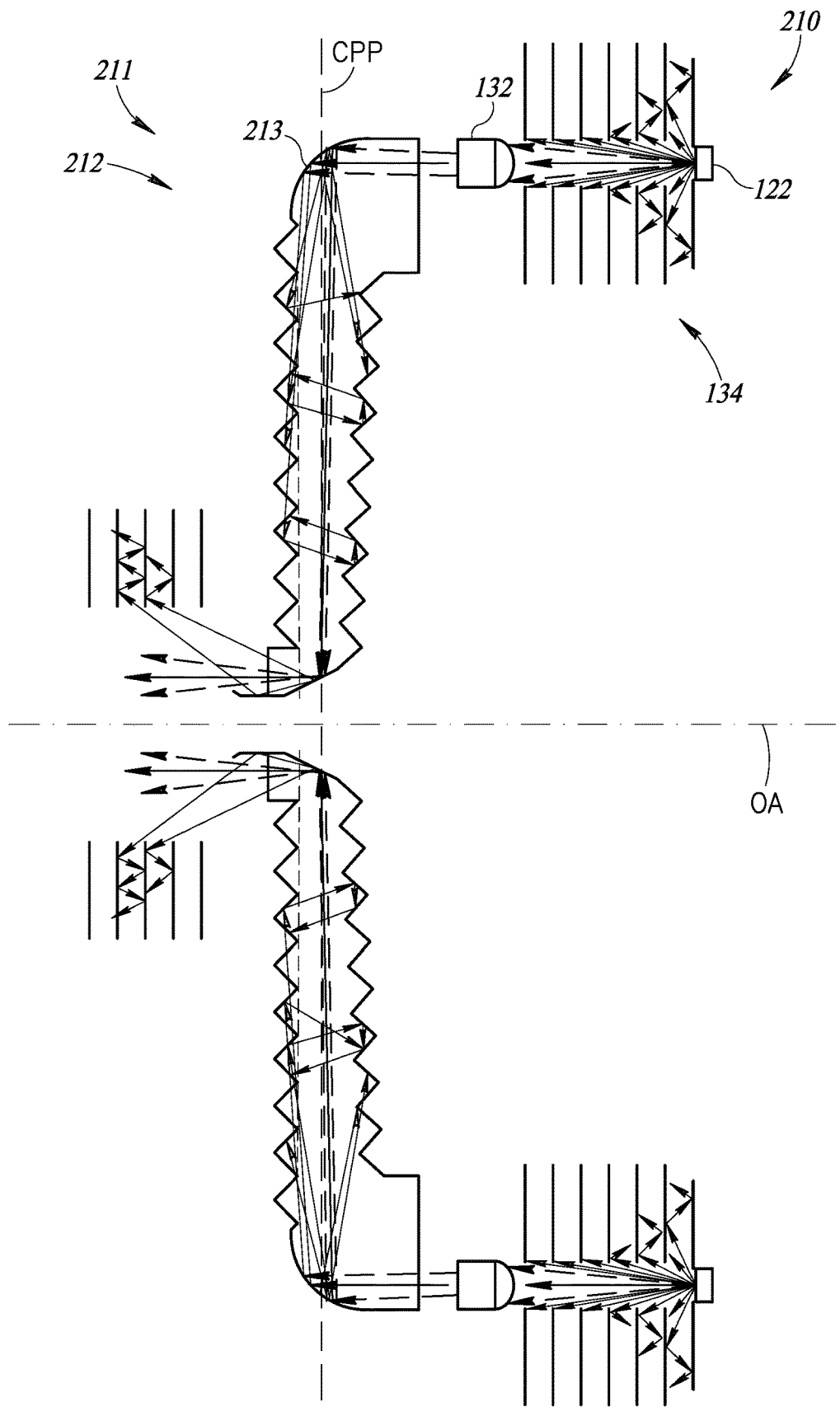
FIG. 13 is a schematic diagram of a fifth embodiment of an annular LED illumination arrangement with illustrative optical rays.

FIG. 13 shows an annular LED illumination arrangement 210 differing from the annular LED illumination arrangement 120 insofar as the latter 210 includes an annular monolithic plastic component 211 acting as an annular folded illumination optical train 212 for emitting illumination co-directional with the optical axis OA and spaced apart therefrom in a direction towards the objective lens 106. Accordingly, the latter 210 includes a primary focusing reflector 213 which is reversed relative to the primary focusing reflector 124.

FIG. 14 to FIG. 21 show eight annular LED illumination arrangements 220A to 220H similar to the annular LED illumination arrangement 120 and differing therefrom insofar as their folded illumination optical trains are constituted by discreet components as opposed to an annular monolithic plastic component. The annular LED illumination arrangements 220A to 220H each includes an annular LED illuminator 121 not shown and a ring of first stage traps 134 not shown. The annular LED illumination arrangements 220A to 220H have similar parts likewise numbered and accordingly identified by their identifying letter A to H. FIG. 14 to FIG. 21 each show an exemplary single illumination ray along an inbound illumination light path from a refractive mini-lens, a discrete primary focusing reflector for reflecting illumination towards a secondary reflector for reflecting illumination towards an objective lens.

Figure 14:
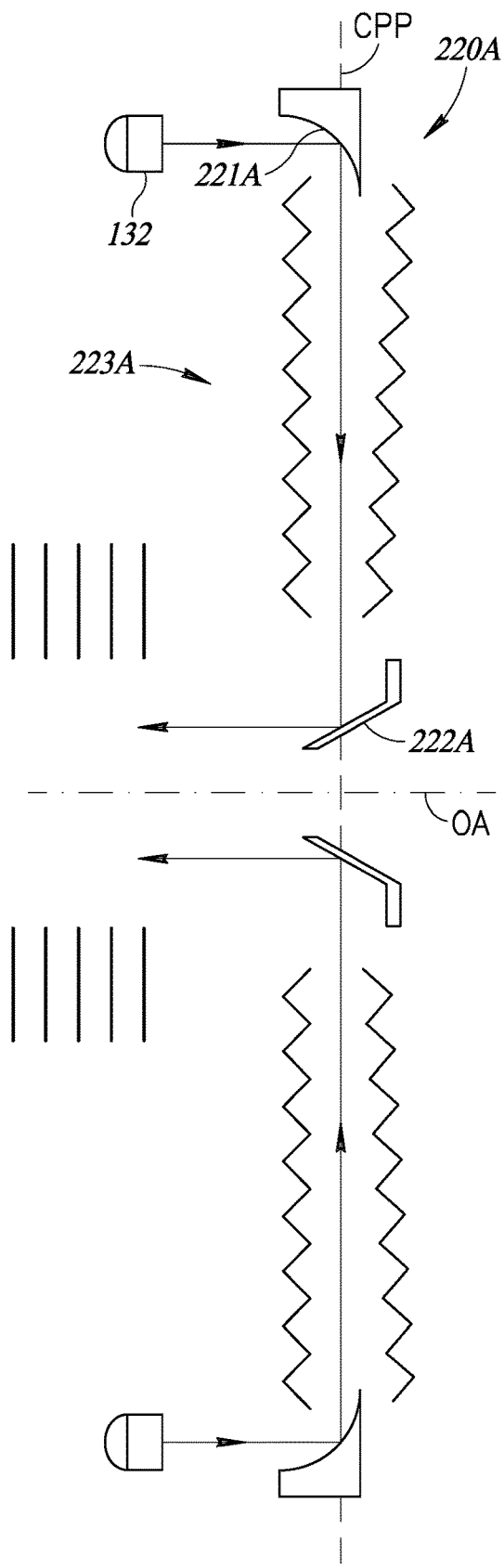
FIG. 14 is a schematic diagram of a sixth embodiment of an annular LED illumination arrangement with illustrative optical rays.

FIG. 14 shows an annular LED illumination arrangement 220A including a discrete annular primary focusing reflector 221A, a discrete annular secondary reflector 222A and a discrete second stage trap 223A between the discrete annular primary focusing reflector 221A and the discrete annular secondary reflector 222A. The discrete second stage trap 223A is similar to the second stage trap 192 in terms of an opposite pair of baffle arrangements.

Figure 15:
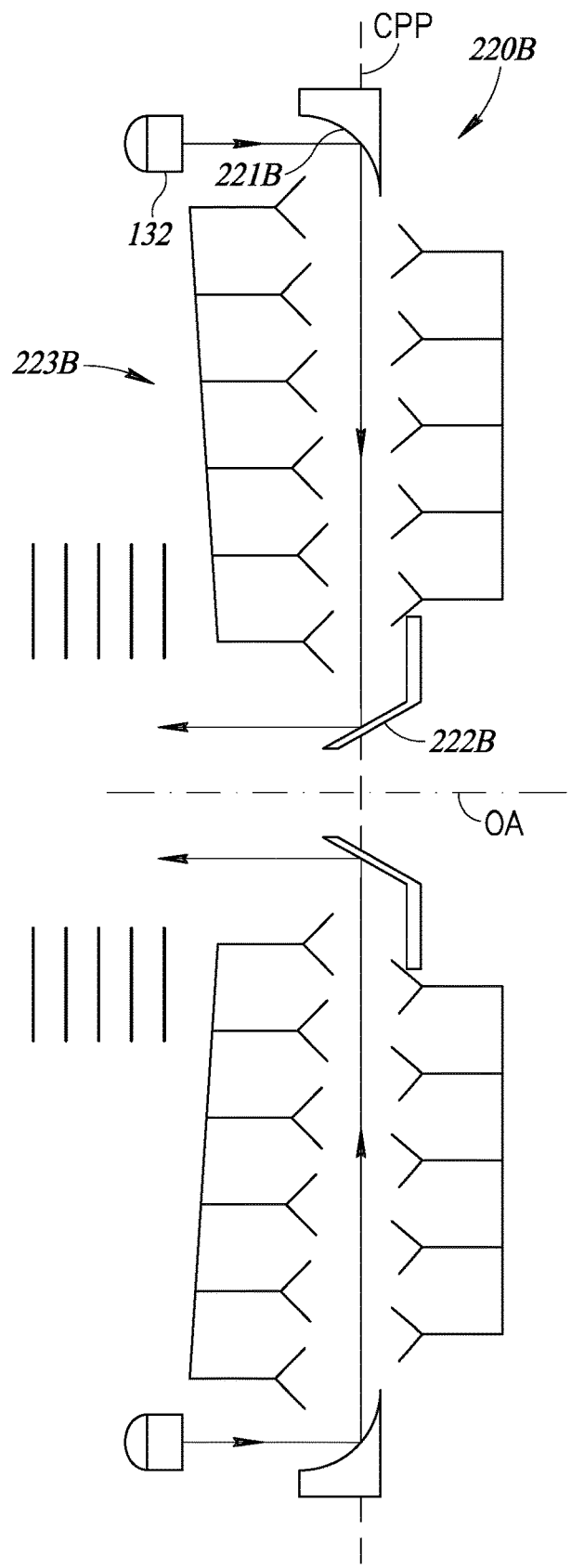
FIG. 15 is a schematic diagram of a seventh embodiment of an annular LED illumination arrangement with illustrative optical rays.
Figure 18:
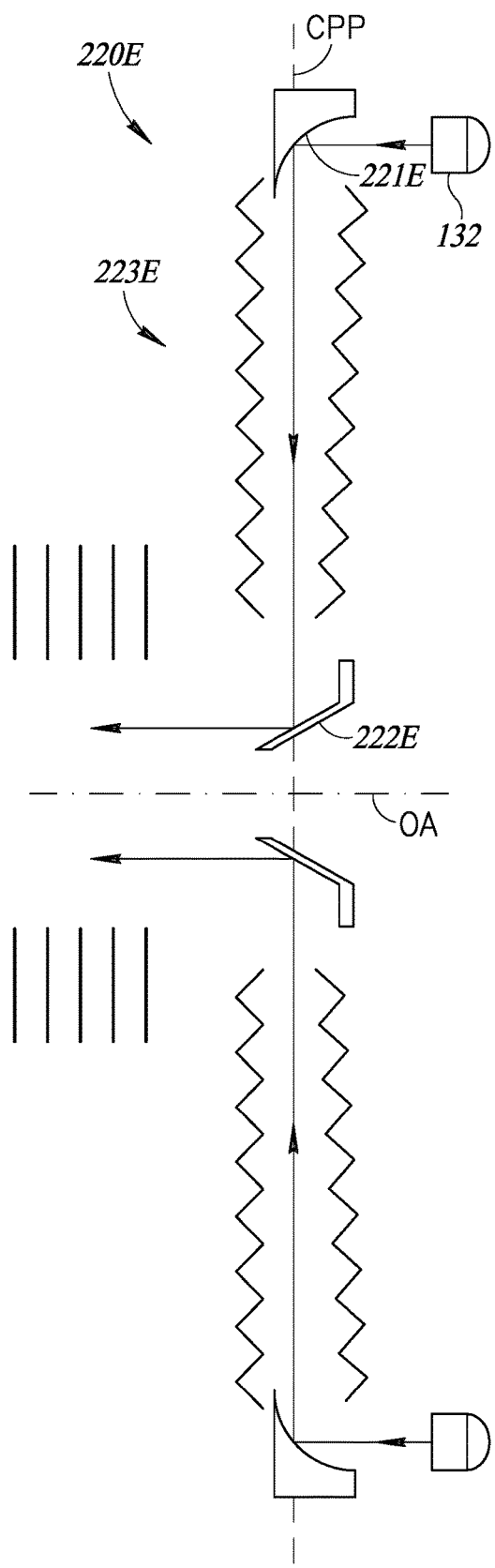
FIG. 18 is a schematic diagram of a tenth embodiment of an annular LED illumination arrangement with illustrative optical rays.
Figure 19:
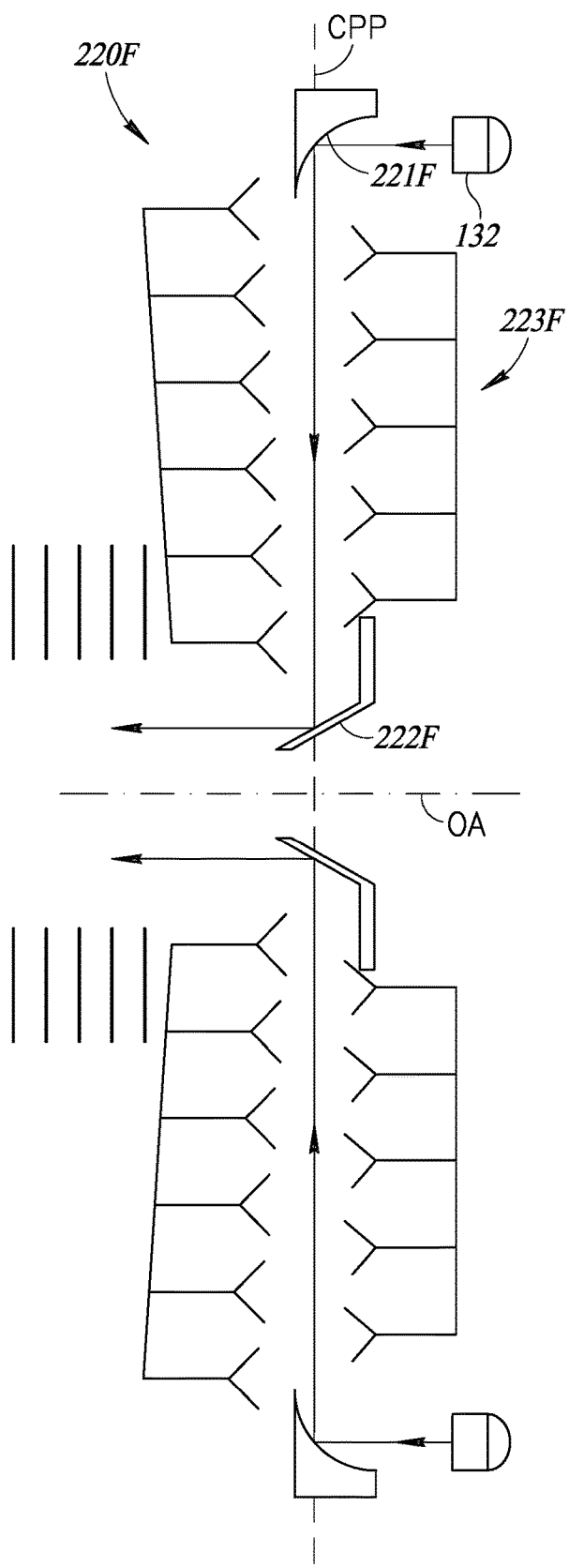
FIG. 19 is a schematic diagram of an eleventh embodiment of an annular LED illumination arrangement with illustrative optical rays.

FIG. 15 shows the annular LED illumination arrangement 220B differs from the annular LED illumination arrangement 220A insofar it includes a discrete second stage trap 223B similar to the annular LED illumination arrangement 170.

FIG. 16 shows the annular LED illumination arrangement 220C differs from the annular LED illumination arrangement 220A insofar it includes a discrete secondary reflector 222C having a lensed surface 224C facing the discrete primary focusing reflector 221C.

FIG. 17 shows the annular LED illumination arrangement 220D differs from the annular LED illumination arrangement 220B insofar it includes a discrete secondary reflector 222D having a lensed surface 224D facing the discrete primary focusing reflector 221D.

FIG. 18 to FIG. 21 shows annular LED illumination arrangements 220E to 220H corresponding to the annular LED illumination arrangements 220A to 220D and differing therefrom insofar as the latter 220E to 220H are intended for use with an annular LED illuminator emitting illumination co-directional with the optical axis OA and spaced apart therefrom in a direction towards an objective lens.

Glare Spot Free Annular LED Illumination Arrangements

Figure 22:
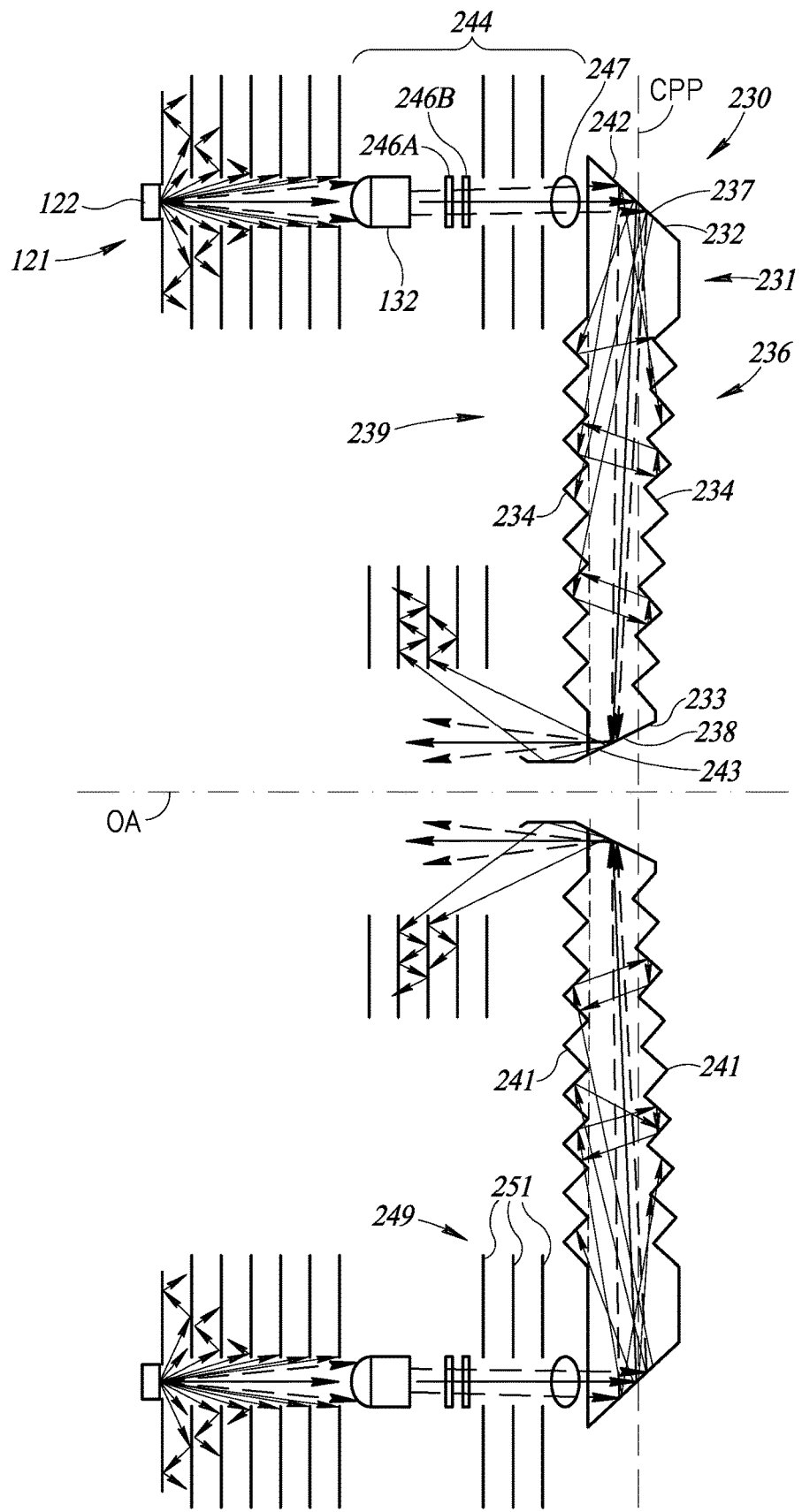
FIG. 22 is a schematic diagram of a first embodiment of a glare spot free annular LED illumination arrangement with illustrative optical rays.

FIG. 22 shows a glare spot free annular LED illumination arrangement 230 including an annular monolithic plastic component 231 similar to the annular monolithic plastic component 127. The annular monolithic plastic component 231 has an outside rim surface 232 generally co-directional with the optical axis OA, an inside rim surface 233 generally co-directional with the optical axis OA and an opposite pair of annular major surfaces 234 extending between the outside rim surface 232 and the inside rim surface 233 and generally perpendicular to the optical axis OA. The annular monolithic plastic component 231 acts an annular folded illumination optical train 236 including a primary focusing reflector 237 formed on the outside rim surface 232 and a secondary reflector 238 formed on the inside rim surface 233. The annular monolithic plastic component 231 also acts as a second stage trap 239 by virtue of the opposite pair of annular major surfaces 234 being formed with concentric ridged surfaces 241. The primary focusing reflector 237 is formed as a primary ring of plane mirror surfaces 242 in registration with the ring of spaced apart individual masked LEDs 122. The primary focusing reflector 237 can employ total internal reflection or mirror coatings. The secondary reflector 238 is formed as a secondary ring of plane mirror surfaces 243 in registration with the primary ring of plane mirror surfaces 242.

The glare spot free annular LED illumination arrangement 230 includes an annular glare spot mask arrangement 244 between the annular arrangement of refractive mini-lenses 132 and the annular folded illumination optical train 236 for removing a glare spot from an objective lens 106. The annular glare spot mask arrangement 244 includes of a ring of at least one glare spot mask 246 per masked LED 122 deployed toward the annular arrangement of refractive mini-lenses 132 and a secondary annular arrangement of refractive mini-lenses 247 deployed away from the annular arrangement of refractive mini-lenses 132. The annular glare spot mask arrangement 244 includes two glare spot masks 246A and 246B per masked LED 122. FIG. 23 shows the elliptical darkened areas 248A and 248B on the glare spot masks 246A and 246B respectively. The glare spot masks 246A and 246B work in conjunction for avoiding glare on an objective lens 106. The annular glare spot mask arrangement 244 also includes a stray illumination trap 249 substantially co-extensive therewith. The stray illumination trap 249 is in the form of a ring of baffle tubes 251 co-directional with the optical axis OA and in registration with the ring of spaced apart individual masked LEDs 122.

The annular LED illumination arrangement 230 results in a circular shaped illumination patch 252 at a digital fundus camera's conjugate retinal plane CRP and the imaged retinal region for each individual masked LED 122. FIG. 24A shows the circular illumination patch 252 illuminated from a 12 o'clock located masked LED 122 at a digital fundus camera's conjugate retinal plane CRP. The circular illumination patch 252 includes a darkened area 253 due to illumination being blocked by the elliptical darkened areas 248A and 248B. The other masked LEDs 122 illuminate overlapping retinal areas according to their positions relative to the 12 o'clock masked LED 122 resulting in an overall illumination pattern image 254 as shown in FIG. 24B.

Figure 25:
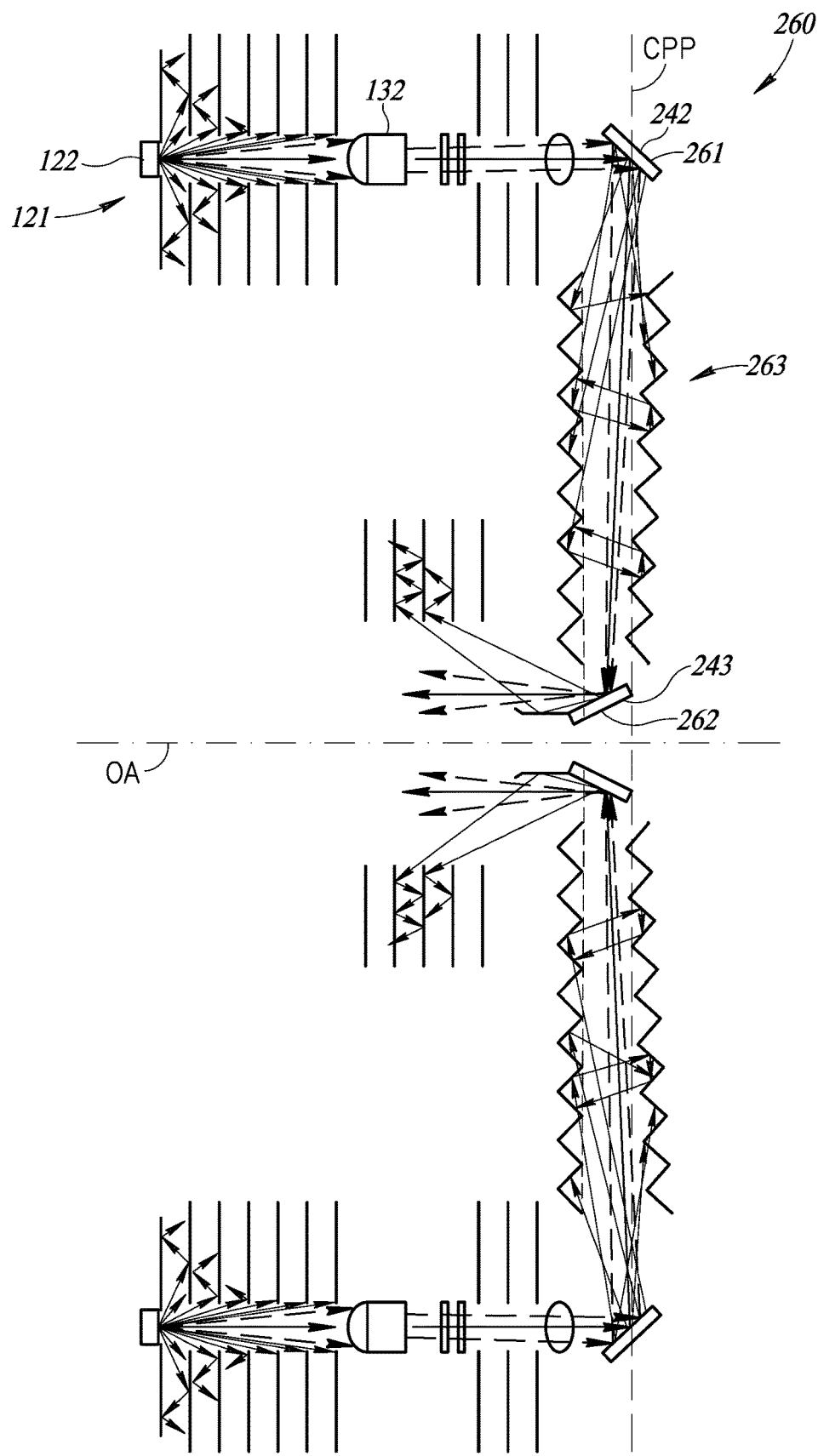
FIG. 25 is a schematic diagram of a second embodiment of a glare spot free annular LED illumination arrangement with illustrative optical rays.

FIG. 25 shows a glare spot free annular LED illumination arrangement 260 similar to the glare spot free annular LED illumination arrangement 230 in terms of glare spot free illumination but differing therefrom insofar that it is made from discrete parts. Accordingly, the annular LED illumination arrangement 260 includes a discrete primary focusing reflector 261, a discrete secondary reflector 262 and a discrete second stage trap 263 instead of the annular monolithic plastic component 231. The discrete primary focusing reflector 261 is formed as a primary ring of plane mirror surfaces 242 in registration with the ring of spaced apart individual masked LEDs 122. The discrete primary focusing reflector 261 can employ total internal reflection or mirror coatings. The discrete secondary reflector 262 is formed as a secondary ring of plane mirror surfaces 243 in registration with the primary ring of plane mirror surfaces 242.

Glare spot free annular LED illumination arrangements can include alternative second stage traps as described hereinabove with reference to FIG. 6 to FIG. 11. Also glare spot free annular LED illumination arrangements can include an annular LED illuminator emitting illumination co-directional with an optical axis and spaced apart therefrom in a direction towards an objective lens as described hereinabove with reference to FIG. 18 to FIG. 21.

While particular embodiments of the present invention are illustrated and described, it would be obvious to those skilled in the art that various other changes and modifications can be made without departing from the spirit and scope of the invention.

The invention claimed is:

1. A digital fundus camera for capturing a digital retinal image of a retinal region of an eye through the eye's pupil, the pupil having an innermost pupillary central area and an outermost pupillary annular surround peripheral to the innermost pupillary central area, the camera comprising:
   (a) a rigid tubular digital fundus camera housing having a leading housing end, a trailing housing end and an inside housing surface;
   (b) an objective lens at said leading housing end,
      said objective lens having an optical axis and a working distance from the eye for imaging the pupil as an imaged pupil at a conjugate pupillary plane and the retinal region as an imaged retinal region at a conjugate retinal plane,
      said objective lens imaging the innermost pupillary central area as an innermost pupillary central area image and the outermost pupillary annular surround as an outermost pupillary annular surround image peripheral to said innermost pupillary central area image;
   (c) an annular LED illumination arrangement at said trailing housing end centered on said optical axis and including:
      (i) an annular LED illuminator having a ring of spaced apart individual masked LEDs each emitting a wide solid angle illumination beam co-directional with said optical axis and spaced apart therefrom,
      ii) an annular folded illumination optical train including a primary focusing reflector for reflecting illumination from said LED illuminator towards a secondary reflector for reflecting illumination towards said objective lens, iii) an annular arrangement of refractive mini-lenses in registration with said ring of spaced apart individual masked LEDs and disposed between said annular LED illuminator and said annular folded illumination optical train for collecting illumination from said annular LED illuminator towards said primary focusing reflector whereby said ring of spaced apart individual masked LEDs are imaged as a ring of spaced apart individual masked LED images at said secondary reflector, and iv) a multiple stage stray illumination trap arrangement for capturing stray illumination from said each masked LED's wide solid angle illumination beam such that said annular LED illumination arrangement emits a ring of narrow solid angle illumination beams towards said objective lens for illuminating the retinal region; and (d) a digital imager at said trailing housing end for capturing the digital retinal image of the retinal region through said annular LED illumination arrangement, the digital fundus camera, in use, with said objective lens being disposed at said working distance from the eye, said conjugate pupillary plane being disposed at said secondary reflector and said ring of narrow solid angle illumination beams being disposed at said outermost pupillary annular surround image whereby said ring of narrow solid angle illumination beams illuminates the retinal region through the outermost pupillary annular surround and said digital imager captures the digital retinal image through said innermost imaged pupillary central area image such that the digital fundus camera separates an inbound illumination light path from said annular LED illumination arrangement to the retinal region from an outbound image forming light path from the retinal region to said digital imager.

2. The camera according to claim 1 wherein said multiple stage stray illumination trap arrangement includes a first stage trap disposed between said LED illuminator and said annular arrangement of refractive mini-lenses,
said first stage trap including a ring of baffle tubes co-directional with said optical axis and in registration with said ring of spaced apart individual masked LEDs, each baffle tube including a stack of staggered annular baffles for capturing stray illumination from said inbound illumination light path emitted by said LED illuminator.

3. The camera according to claim 1 wherein said multiple stage stray illumination trap arrangement includes a second stage trap centered on said optical axis and disposed between said primary focusing reflector and said secondary reflector,
said second stage trap including an opposite pair of baffle arrangements for capturing stray illumination from said inbound illumination light path reflected by said primary focusing reflector.

4. The camera according to claim 3 wherein said opposite pair of baffle arrangements is constituted by concentric arrangement of ridged surfaces.

5. The camera according to claim 3 wherein said opposite pair of baffle arrangements is constituted by an opposite pair of annular baffle devices centered on said optical axis and having concentric arrangements of compartments.

6. The camera according to claim 1 wherein said multiple stage stray illumination trap arrangement includes a third stage trap disposed between said secondary reflector and said objective lens and adjacent said secondary reflector, said third stage trap including a baffle tube centered on said optical axis,
said baffle tube including a stack of staggered annular baffles for capturing stray illumination from said inbound illumination light path reflected by said secondary reflector.

7. The camera according to claim 6 wherein said baffle tube further includes a cylindrical deflector flange extending from said secondary reflector towards said objective lens, said deflector flange being angled outwards with respect to said optical axis for deflecting stray illumination into said third stage trap's baffle tube.

8. The camera according to claim 1 wherein said inside housing surface between said leading housing end and said trailing housing end includes a stack of staggered annular baffles centered on said optical axis for acting as a supplementary stray illumination trap to said multiple stage stray illumination trap.

9. The camera according to claim 1 and further comprising a an annular glare spot mask arrangement between said annular arrangement of refractive mini-lenses and said annular folded illumination optical train for removing a glare spot from said objective lens,
said annular glare spot mask arrangement including a ring of at least one glare spot mask deployed toward said annular arrangement of refractive mini-lenses and a secondary annular arrangement of refractive mini-lenses deployed away from said annular arrangement of refractive mini-lenses.

10. The camera according to claim 9 wherein said annular glare spot mask arrangement further includes a fourth stage trap substantially co-extensive therewith,
said fourth stage trap including a ring of baffle tubes co-directional with said optical axis and in registration with said ring of spaced apart individual masked LEDs.

11. The camera according to claim 1 wherein said folded illumination optical train is constituted by an annular monolithic plastic component including:
i) an outside rim surface generally co-directional with said optical axis and spaced apart therefrom, and including said primary focusing reflector,
ii) an inside rim surface generally co-directional with said optical axis and spaced apart therefrom, and including said secondary reflector, and
iii) an opposite pair of annular major surfaces extending between said outside rim surface and said inside rim surface and generally perpendicular to said optical axis and constituting said second stage trap.

12. The camera according to claim 11 and further comprising an outside flange including said outside rim surface having said primary focusing reflector, an inside flange including said inside rim surface having said secondary reflector, and an intermediate illumination venting section between said outside flange and said inside flange,
said intermediate illumination venting section includes at least a leading truncated conical shaped leading illumination vent having a leading annular major surface generally perpendicular to said optical axis and a leading peripheral surface extending between said leading annular major surface and said outside flange and said inside flange whereby stray illumination exits from said intermediate illumination venting section through said leading peripheral surface into said digital fundus camera housing for absorption therein.

13. The camera according to claim 12 wherein said annular monolithic plastic component includes said annular arrangement of refractive mini-lenses.

14. The camera according to claim 1 wherein said folded illumination optical train is constituted by discrete components including a discrete primary focusing reflector and a discrete secondary reflector.

15. The camera according to claim 1 wherein said primary focusing reflector is constituted by a primary ring of plane mirror surfaces in registration with said ring of spaced apart individual masked LED and said secondary reflector is constituted by a secondary ring of plane mirror surfaces in registration with said primary ring of plane mirror surfaces.

16. The camera according to claim 1 wherein said annular LED illuminator emits illumination co-directional with the optical axis and spaced apart therefrom in an opposite direction to said objective lens.

17. The camera according to claim 1 wherein said annular LED illuminator emits illumination co-directional with the optical axis and spaced apart therefrom in a direction towards said objective lens.

* * * * *